US012758089B2

(12) United States Patent
Jia et al.

(10) Patent No.: US 12,758,089 B2
(45) Date of Patent: Oct. 13, 2026

(54) THREE-DIMENSIONAL LIGHT-FIELD MICROENDOSCOPY WITH A GRIN LENS ARRAY

(71) Applicant: GEORGIA TECH RESEARCH CORPORATION, Atlanta, GA (US)

(72) Inventors: Shu Jia, Johns Creek, GA (US); Tara Urner, Atlanta, GA (US); Andrew Inman, Atlanta, GA (US); Benjamin Lapid, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 154 days.

(21) Appl. No.: 18/714,524

(22) PCT Filed: Dec. 2, 2022

(86) PCT No.: PCT/US2022/051698
§ 371 (c)(1),
(2) Date: May 29, 2024

(87) PCT Pub. No.: WO2023/102213
PCT Pub. Date: Jun. 8, 2023

(65) Prior Publication Data

US 2025/0040796 A1 Feb. 6, 2025

Related U.S. Application Data

(60) Provisional application No. 63/285,551, filed on Dec. 3, 2021.

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00057* (2013.01); *G02B 3/0056* (2013.01);
(Continued)

(58) Field of Classification Search
CPC ... A61B 1/07; A61B 1/00057; A61B 1/00193; A61B 1/00194; A61B 1/002;
(Continued)

(56) References Cited

U.S. PATENT DOCUMENTS 5,926,319 A * 7/1999 Phillips ................ G02B 3/0056 359/620
2005/0192480 A1* 9/2005 Toriya ................ A61B 1/00167 600/128

(Continued)

OTHER PUBLICATIONS

International Search Report and Written Opinion received in PCT/US2022/051698 mailed Mar. 10, 2023.

(Continued)

*Primary Examiner* — Michael J Carey
*Assistant Examiner* — Dayton Hyun Jin Barker
(74) *Attorney, Agent, or Firm* — Meunier Carlin & Curfman LLC

(57) ABSTRACT

An optical microendoscopy includes an endoscopic probe that has a plurality of integrated fiber optics for uniform illumination and an array of gradient index (GRIN) lenses. The GRIN lenses are configured to capture a reflected light field from one or more on-axis sampling of the reflected light field and two or more off-axis sampling of the reflected light field.

17 Claims, 21 Drawing Sheets

(51) Int. Cl.
*G02B 3/00* (2006.01)
*G02B 23/24* (2006.01)

(52) U.S. Cl.
CPC ......... *G02B 3/0087* (2013.01); *G02B 23/243* (2013.01); *G02B 23/2469* (2013.01)

(58) Field of Classification Search
CPC .. G02B 3/0056; G02B 3/0087; G02B 23/243; G02B 23/2469
See application file for complete search history.

(56) References Cited

U.S. PATENT DOCUMENTS

| | | | | |
|---|---|---|---|---|
| 2006/0041192 | A1* | 2/2006 | Klootz | A61B 1/07 600/178 |
| 2009/0054791 | A1* | 2/2009 | Flusberg | A61B 5/0059 600/478 |
| 2014/0086530 | A1* | 3/2014 | Benjamin | G02B 6/322 29/428 |
| 2016/0151055 | A1* | 6/2016 | Leblond | A61B 5/1459 600/478 |
| 2017/0219999 | A1* | 8/2017 | Serabyn | G02B 6/0008 |
| 2018/0372633 | A1 | 12/2018 | Yamazoe et al. | |
| 2019/0167081 | A1* | 6/2019 | Hillman | G02B 21/0076 |
| 2019/0174038 | A1* | 6/2019 | Takeuchi | G02B 23/2461 |
| 2022/0385848 | A1* | 12/2022 | Venkataraman | G06T 11/60 |
| 2023/0280526 | A1* | 9/2023 | Gregg | G02B 6/02042 |

OTHER PUBLICATIONS

Ali, et al., "First Intraoperative Experience With Three-dimensional (3D) High-definition (HD) Nasal Endoscopy for Lacrimal Surgeries", European Archives of Oto-Rhino-Laryngology, vol. 274, No. 5, pp. 2161-2164, May 2017.

Bedard, et al., "Light Field Otoscope Design for 3D In Vivo Imaging of the Middle Ear", Biomedical Optics Express, vol. 8, No. 1, pp. 260-272, Dec. 14, 2016.

Boulocher, et al., "Non-Invasive In Vivo Quantification of the Medial Tibial Cartilage Thickness Progression in an Osteoarthritis Rabbit Model With Quantitative 3D High Resolution Micro-MRI", Osteoarthritis and Cartilage, vol. 15, No. 12, pp. 1378-1387, Dec. 2007.

Curro, et al., "Three-Dimensional (3D) Versus Two-Dimensional (2D) Laparoscopic Bariatric Surgery: A Single-Surgeon Prospective Randomized Comparative Study", Obesity Surgery, vol. 25, No. 11, pp. 2120-2124, Nov. 2015.

D'Haens, et al., "Fully Endoscopic Transsphenoidal Surgery for Functioning Pituitary Adenomas: A Retrospective Comparison With Traditional Transsphenoidal Microsurgery in the Same Institution", Surgical Neurology, vol. 72, No. 4, pp. 336-340, Oct. 2009.

Guo, et al., "3D Light-Field Endoscopic Imaging Using a Grin Lens Array", Applied Physics Letters, vol. 116, No. 10, pp. 101105-1-101105-5, 2020.

Hassanfiroozi, et al., "Hexagonal Liquid Crystal Lens Array for 3D Endoscopy", Optics Express, vol. 23, No. 2, pp. 971-981, 2015.

Hassanfiroozi, et al., "Liquid Crystal Lens Array for 3d Endoscope Application", Proceedings of SPIE vol. 9117, pp. 91170E-1-91170E-7, 2014.

Hyun, et al., "Feasibility of Obtaining Quantitative 3-dimensional Information Using Conventional Endoscope: A Pilot Study", Clinical Endoscopy, vol. 45, No. 3, pp. 182-188, 2012.

Kaltenbach, et al., "Use of the Colonoscope Training Model with the Colonoscope 3D Imaging Probe Improved Trainee Colonoscopy Performance: A Pilot Study", Digestive Diseases and Sciences, vol. 56, No. 5, pp. 1496-1502, May 2011.

Kampschulte, et al., "Quantitative 3D Micro-CT Imaging of Human Lung Tissue", Rofo, vol. 185, No. 9, pp. 869-876, 2013.

Levoy, et al., "Light Field Microscopy", ACM Transactions on Graphics, vol. 25, No. 3, pp. 1-11, 2006.

Levoy, et al., "Recording and Controlling the 4D Light Field in a Microscope Using Microlens Arrays", Journal of Microscopy, vol. 235, No. 2, pp. 144-162, Aug. 2009.

Lin, et al., "Speckle Illumination Holographic Non-Scanning Fluorescence Endoscopy", Journal of Biophotonics, vol. 11, No. 11, Article No. e201800010, pp. 1-7, Nov. 2018.

Maier-Hein, et al., "Optical Techniques for 3D Surface Reconstruction in Computer-assisted Laparoscopic Surgery", Medical Image Analysis, vol. 17, No. 8, pp. 974-996, Dec. 2013.

Moore, D T, "Gradient-Index Optics: A Review", Applied Optics, vol. 19, No. 7, pp. 1035-1038, Apr. 1, 1980.

Nakagawa, et al., "Quantitative Depth Analysis of Optic Nerve Head Using Stereo Retinal Fundus Image Pair", Journal of Biomedical Optics, vol. 13, No. 6, pp. 064026-1-064026-10, 2008.

Ng, et al., "Light Field Photography with a Hand-held Plenoptic Camera", Stanford University Computer Science Tech Report, pp. 1-11, 2005.

Nomura, et al., "Comparison of 3D Endoscopy and Conventional 2D Endoscopy in Gastric Endoscopic Submucosal Dissection: an Ex Vivo Animal Study", Surgical Endoscopy, vol. 33, No. 12, Dec. 2019, pp. 4164-4170.

Orth, et al., "Optical Fiber Bundles: Ultra-Slim Light Field Imaging Probes", Science Advances, vol. 5, No. 4, pp. 1-10, Apr. 26, 2019.

Rotenberg, et al., "Microscopic Versus Endoscopic Pituitary Surgery: A Systematic Review", Laryngoscope, vol. 120, No. 7, pp. 1292-1297, Jul. 2010.

Sahu, et al., "3D Laparoscopy—Help or Hype; Initial Experience of a Tertiary Health Centre", Journal of Clinical and Diagnostic Research, vol. 8, No. 7, pp. NC01-NC03, Jul. 2014.

Singh, et al., "Three-Dimensional Endoscopy in Sinus Surgery", Current Opinion in Otolaryngology & Head and Neck Surgery, vol. 21, No. 1, pp. 3-10, Feb. 2013.

Sinha, et al., "3D Laparoscopy: Technique and Initial Experience in 451 Cases", Gynecological Surgery, vol. 10, pp. 123-128, Jan. 22, 2013.

Smith, et al., "Effect of Passive Polarizing Three-dimensional Displays on Surgical Performance for Experienced Laparoscopic Surgeons", British Journal of Surgery, vol. 101, No. 11, pp. 1453-1459, Oct. 2014.

Spille, et al., "2D Versus 3D in Laparoscopic Surgery by Beginners and Experts: A Randomized Controlled Trial on a Pelvitrainer in Objectively Graded Surgical Steps", Journal of Surgical Education, vol. 74, No. 5, pp. 867-877, 2017.

Sun, et al., "The Measurement of Refractive Index Profile and Aberration of Radial Gradient Index Lens by Using Imaging Method", Optics & Laser Technology, vol. 36, No. 2, pp. 163-166, Mar. 2004.

Tokas, et al., "Impact of Three-Dimensional Vision in Laparoscopic Partial Nephrectomy for Renal Tumors", Turkish Journal of Urology, vol. 47, No. 2, pp. 144-150, Mar. 2021.

Vasudevan, et al., "The Role of Three-Dimensional Endoscopy in Pituitary Adenoma Surgery", Neurosurgery Clinics of North America, vol. 30, No. 4, pp. 421-432, Oct. 2019.

Wang, et al., "Extended Depth-of-Field 3D Endoscopy With Synthetic Aperture Integral Imaging Using an Electrically Tunable Focal-length Liquid-Crystal Lens", Optics Letters vol. 40, No. 15, pp. 3564-3567, 2015.

Zhu, et al., "Optical Design and Development of a Snapshot Light-Field Laryngoscope", Optical Engineering, vol. 57, No. 2, pp. 023110-1-023110-5, Feb. 2018.

* cited by examiner

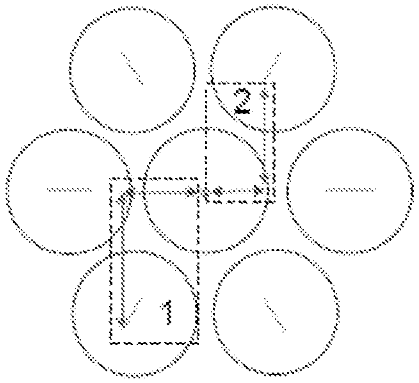
FIG. 4(a)
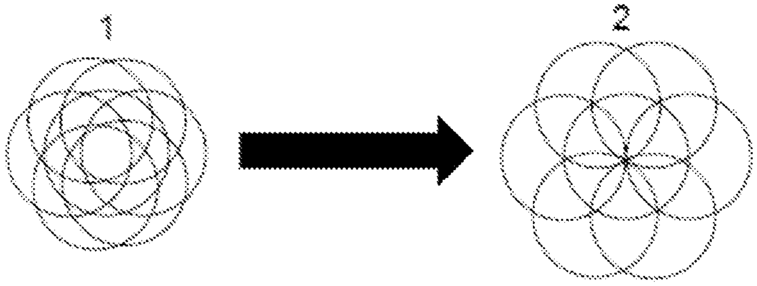
FIG, 4(b)

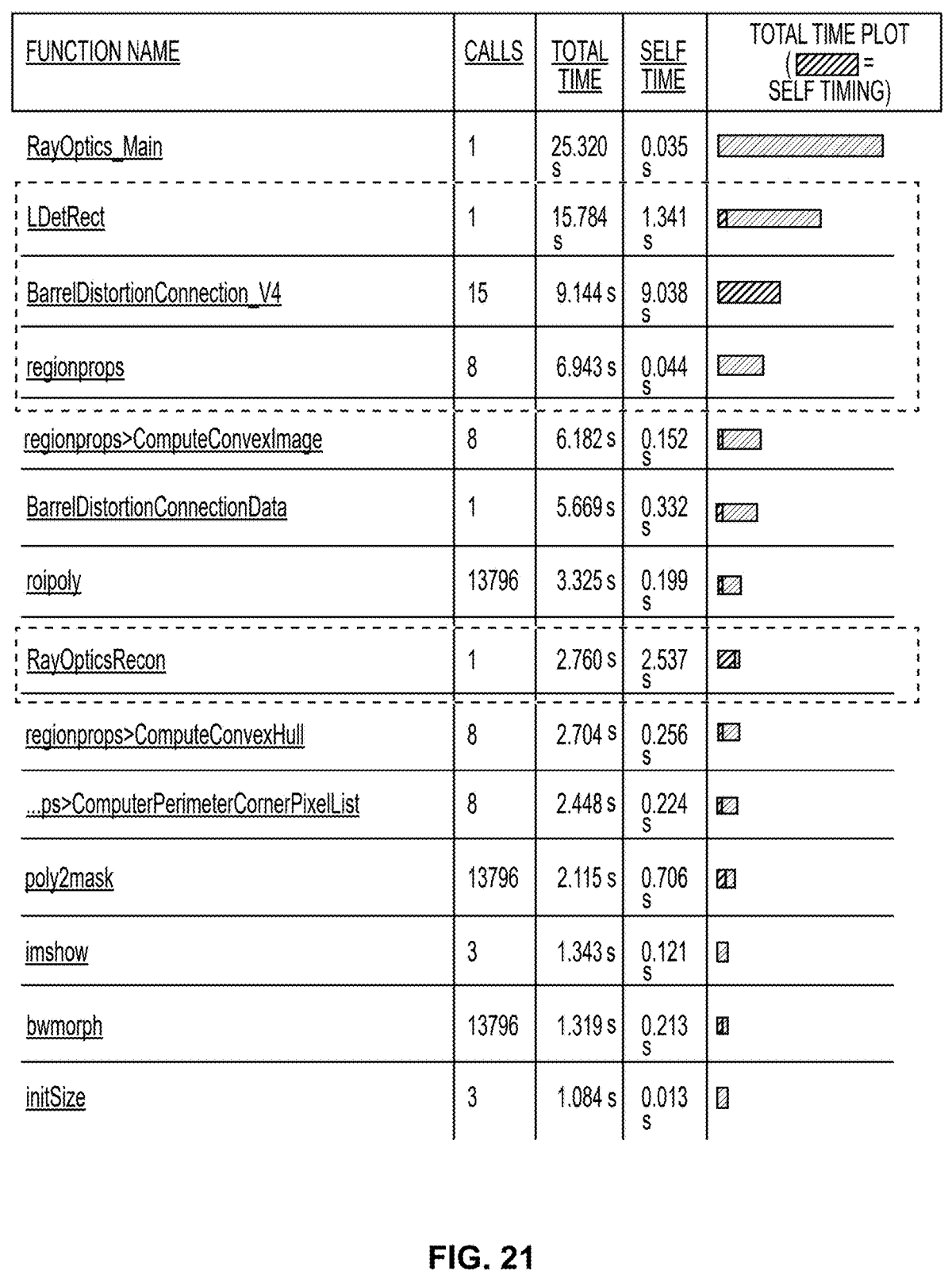

| FUNCTION NAME | CALLS | TOTAL TIME | SELF TIME | TOTAL TIME PLOT (▨ = SELF TIMING) |
|---|---|---|---|---|
| RayOptics_Main | 1 | 25.320 s | 0.035 s | |
| LDetRect | 1 | 15.784 s | 1.341 s | |
| BarrelDistortionConnection_V4 | 15 | 9.144 s | 9.038 s | |
| regionprops | 8 | 6.943 s | 0.044 s | |
| regionprops>ComputeConvexImage | 8 | 6.182 s | 0.152 s | |
| BarrelDistortionConnectionData | 1 | 5.669 s | 0.332 s | |
| roipoly | 13796 | 3.325 s | 0.199 s | |
| RayOpticsRecon | 1 | 2.760 s | 2.537 s | |
| regionprops>ComputeConvexHull | 8 | 2.704 s | 0.256 s | |
| ...ps>ComputerPerimeterCornerPixelList | 8 | 2.448 s | 0.224 s | |
| poly2mask | 13796 | 2.115 s | 0.706 s | |
| imshow | 3 | 1.343 s | 0.121 s | |
| bwmorph | 13796 | 1.319 s | 0.213 s | |
| initSize | 3 | 1.084 s | 0.013 s | |

FIG. 21

THREE-DIMENSIONAL LIGHT-FIELD MICROENDOSCOPY WITH A GRIN LENS ARRAY

CROSS-REFERENCE TO RELATED APPLICATIONS

This application is a U.S. National Stage application filed under 35 U.S.C. § 371 of PCT/US2022/051698 filed Dec. 2, 2022, which claims priority to, and the benefit of U.S. Provisional Application No. 63/285,551 filed Dec. 3, 2021, each of which is incorporated herein by reference in their entirety.

BACKGROUND

Field

Embodiments of the present invention relate to microendoscopy, specifically, a Three Dimensional Light-Field Microendoscopy with a GRIN Lens array.

Background

Optical endoscopy has emerged as an indispensable clinical tool for modern minimally invasive surgery. Most endoscopy systems primarily capture a 2D projection of the 3D surgical field. Currently available 3D endoscopes can restore stereoscopic vision directly by projecting laterally shifted views of the operating field to each eye through 3D glasses. These tools provide surgeons with informative 3D visualizations, but they do not enable quantitative volumetric rendering of tissue, nor do they provide quantitative depth perception, effective anatomic landmark recognition, and efficient learning curve for trainees. Therefore, advanced tools are desired to quantify tissue tomography for high precision microsurgery or medical robotics. Accordingly, there is a need for a device that provides the surgeon with the depth perception that they need, especially surgeons in surgical areas with in-depth extension, vascular encasement, or dense tumor structures.

BRIEF SUMMARY OF THE DISCLOSURE

Accordingly, the present invention is directed to Three Dimensional Light-Field Microendoscopy with a GRIN Lens array that obviates one or more of the problems due to limitations and disadvantages of the related art.

An advantage of the present invention is to provide an endoscopic imaging platform that allows for real-time, quantitative 3D anatomical visualization and interpretation during complex procedures.

In accordance with the purpose(s) of this invention, as embodied and broadly described herein, this invention, in one aspect, relates to a microendscopy system. The system in based on an endoscopic probe. The probe has a plurality of integrated fiber optics for uniform illumination and an array of gradient index (GRIN) lenses configured to capture a reflected light field from one or more on-axis sampling of the reflected light field and two or more off-axis sampling of the reflected light field.

In the microendscopic system or probe: The captured reflected light field may include 6 off-axis samples. The plurality of integrated fiber optics may include 3 or more fibers embedded within an endoscopic probe core, each having an illumination output. Each of the fiber optics may include an illumination output at an end of the endoscopic probe, wherein the illumination outputs are distributed equally at the end of the endoscopic probe. In an aspect, the GRIN lens array may have 6 GRIN lenses. The 6 GRIN lenses may be positioned in a hexagonal array at an end of the endoscopic probe. The probe may further include an illumination output of one of the integrated fiber optics at a center of the hexagonal array at the end of the endoscopic probe. The GRIN lenses of the GRIN lens array may alternate with illumination outputs of individual ones of the integrated fiber optic at an end of the endoscopic probe. The system may include an image processing unit configured to receive the reflected light field from the endoscopic probe to reconstruct an image using a ray-optics reconstruction operation. A first subset of the GRIN lenses in the array may have a first property and wherein a second subset of the GRIN lenses in the array may have a second property different from the first. The system or probe may include a third subset of GRIN lenses having a third property different from the first property and the second property. The fiber optics may include LED light sources.

According to principles described herein, the point-spread function (PSF) calibration may involve fitting an experimental depth-dependent magnification function M(z) with a ray-optics model of magnification. The system or probe may further include a coherent light source and a camera for receiving reflected laser light.

A method of performing microendoscopy according to the principles described herein includes providing illumination from an end of an endoscopic probe, the endoscopic probe having a plurality of integrated fiber optic illumination sources for uniform illumination; capturing a reflected light field, for light-field imaging, through an array of gradient index (GRIN) lenses, including (i) one or more on-axis sampling of the reflected light field and (ii) two or more off-axis sampling of the reflected light field; and reconstructing an image via a reconstruction algorithm using (i) the one or more on-axis sampling of the reflected light field and (ii) the two or more off-axis sampling of the reflected light field. The method may further include further providing a laser light source from the end of the endoscope and performing laser speckle contrast imaging (LSCI) using reflection of light provided by the laser light source.

Further embodiments, features, and advantages of the Three Dimensional Light-Field Microendoscopy with GRIN Lens array, as well as the structure and operation of the various embodiments of the Three Dimensional Light-Field Microendoscopy with GRIN Lens array, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate Three Dimensional Light-Field Microendoscopy with GRIN Lens array. Together with the description, the figures further serve to explain the principles of the Three Dimensional Light-Field Microendoscopy with GRIN Lens array described herein and thereby enable a person skilled in the pertinent art to make and use the Three Dimensional Light-Field Microendoscopy with GRIN Lens array.

FIG. 1 includes subparts (a), (b), and (c).

FIG. 2(*b*) is a cutaway rendering of a GLAM according to the principles described herein.

FIGS. 4(*a*) and 4(*b*) illustrate the compensation of shift in z.

FIG. 6(*b*) illustrate example relays for use with the devices described herein.

FIG. 8(*b*) shows an axial stack projection (step size=50 μm) of the RGB PSF within an axial range of 22 mm.

FIG. 8(*c*) shows a projection of the PSF shift from the lens center for each elemental image along the y-z axis.

FIG. 21 illustrates a comparison of actual reconstruction according to a prototype (RayOpticsRecon) of the presently described device with respect to other devices.

DETAILED DESCRIPTION

Figure 1:
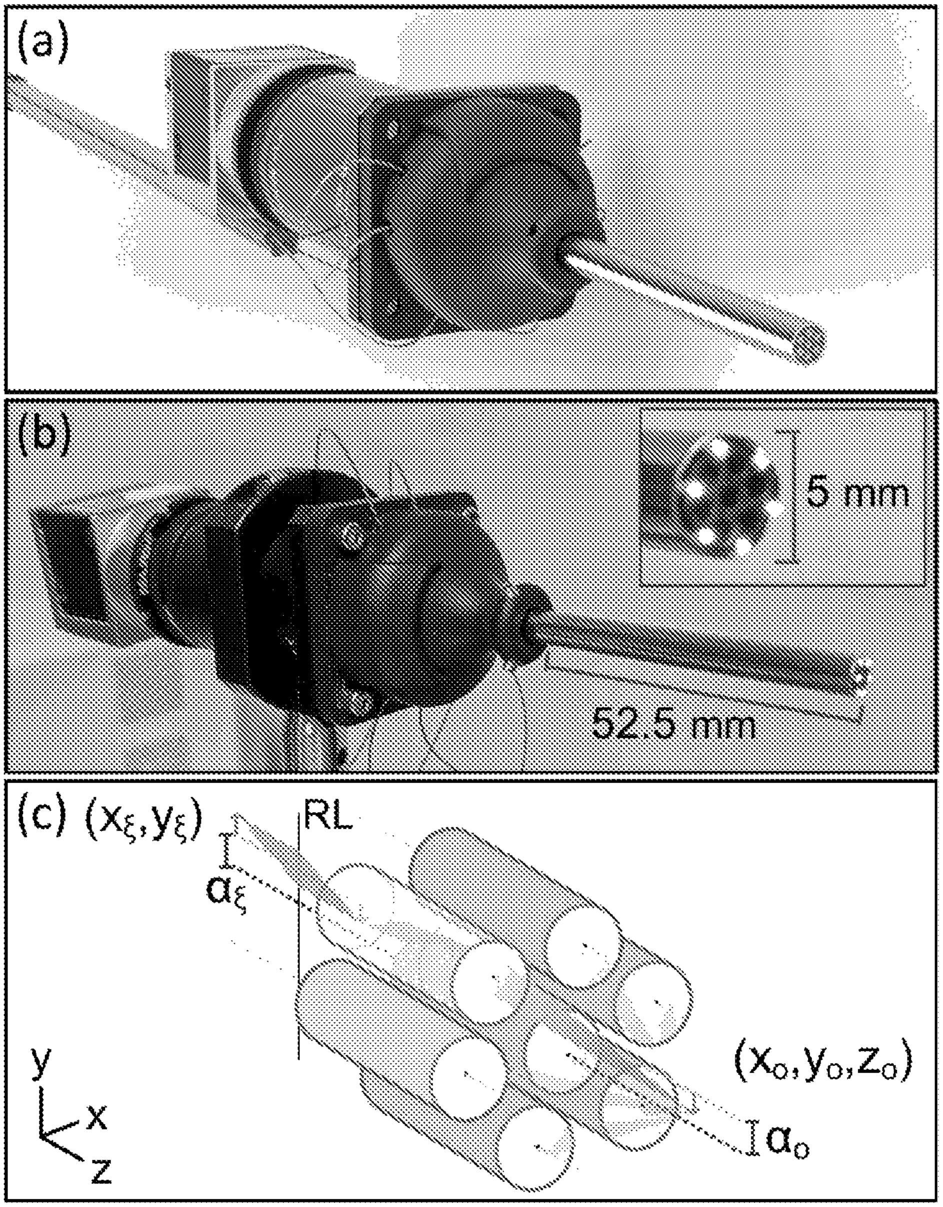
FIG. 1 shows a CAD model, a photograph, and a schematic of a prototype according to the principles described herein.

Reference will now be made in detail to embodiments of the Three Dimensional Light-Field Microendoscopy with GRIN Lens array with reference to the accompanying figures. The same reference numbers in different drawings may identify the same or similar elements.

It will be apparent to those skilled in the art that various modifications and variations can be made in the present invention without departing from the spirit or scope of the invention. Thus, it is intended that the present invention cover the modifications and variations of this invention, provided they come within the scope of the appended claims and their equivalents.

Light-field imaging suggests itself as a promising solution to the challenge. The approach can capture both the spatial and angular information of optical signals, permitting the computational synthesis of the 3D volume of an object. Presented herein is GRIN lens array microendoscopy (GLAM) as a single-shot, full-color, and quantitative 3D microendoscopy system. GLAM contains integrated fiber optics for illumination and a GRIN lens array to capture the reflected light field. The system can provide a 3D resolution of ~100 μm over an imaging depth of ~22 mm and a field of view up to 1 $cm^2$. GLAM maintains, in some embodiments, a small form factor consistent with the clinically desirable design, making the system readily translatable to a clinical prototype.

GLAM can be configured, in some embodiments, as a compact, single-shot, full-color, and quantitative 3D microendoscopy system. By subsampling the angular component of the light field, we gain access to the axial dimension, achieving a 3D resolution of ~100 μm over an imaging depth of ~22 mm and a field of view up to ~1 $cm^2$. The system can incorporate a GRIN lens array instead of the two-lens stereoscopic scheme, promising an alternative paradigm for clinical applications requiring high-resolution, quantitative volumetric measurements. GLAM exhibits a small form factor, a prototype readily translatable to further preclinical and clinical testing.

Specifically, in some embodiments, the system PSF is used for pre-calibration of the 3D reconstruction algorithm. This has the advantages of 1) considering misalignments or other experimental anomalies and 2) making the quantitative 3D reconstruction sample-independent. One current limitation of the PSF calibration approach is that it assumes a nominal lens separation of 1.4 mm. This may be slightly different between each lens due to inhomogeneities in the 3D-printed core. Future versions of the analysis software could address this by calibrating the lens pitch directly to the GLAM system. Also, this may improve the estimation of the PSF offset and GRIN-to-relay spacing. For the reconstruction, speeds of ~0.9 seconds per millimeter have been obtained over multiple millimeters of depth without any further optimization of the algorithm or processing hardware. Through the use of a GPU and optimization of the reconstruction algorithm to fully utilize this hardware, the reconstruction algorithm should be able to obtain video-rate real-time 3D imaging and visualization.

The use of the GRIN lens array (GLA) enables quantitative depth estimation and allows for simple chromatic calibration for accurate RGB depth encoding. The pinhole image offsets in the off-axis elemental images provide a quick readout for axial chromatic aberrations in the GLA, which has been incorporated into the system magnification function M(z). Traditionally, this information would be obtained through a more complicated imaging protocol involving scanning optics and a fluorescent sample. In contrast, this calibration method offers a fast readout of axial aberrations suitable for incorporating into the downstream analysis.

The 3D reconstruction obtained with the GLAM system demonstrates robust axial sectioning capability and shows recovered depth information about opaque, reflective samples on the microscale. Notably, the GLA assembly used in this system can be used as a blueprint that is readily reconfigurable and scalable by altering the pitch and focal distance of the system to match desired applications. Additionally, GRIN-to-relay spacing or additional relay lenses can tune the magnification function as needed. Increasing the pitch will improve axial resolution with the trade-off of a smaller field of view and a more prominent form factor, while decreasing the pitch has the opposite effect. An exemplary effect of adjusting GRIN-to-relay spacing can be seen in FIG. 4.

The use of integrated illumination is another characteristic that makes the endoscope system viable for practical use. Around the GRIN lens array are six optical fibers, which provide uniform illumination to the area in front of the endoscope. A computer can continuously control the intensities of the illumination to provide the appropriate amount of lighting for data sampling.

The properties, including the high 3D resolution, full-color acquisition, and computational simplicity, promise GLAM for future advancement and realization for surgical procedures. Furthermore, the system offers the potential to integrate quantitative 3D imaging with other devices, such as surgical robotics, to conduct more accurate automated 3D navigation within tight spaces in the body. Such a strategy for microimaging in three dimensions could be extended beyond the medical realm for general engineering and manufacturing purposes.

An optical microscopy system may include an endoscopic probe that has a plurality of integrated fiber optics for uniform illumination, and a gradient index (GRIN) lens array configured to capture a reflected light field (e.g., for light-field imaging) from one or more on-axis sampling of the reflected light field (e.g., 1) and two or more off-axis sampling of the reflected light field (e.g., 6). The plurality of integrated fiber optics may include 3 or more fibers (e.g., 6) embedded within an endoscopic probe core. The system may further include an image processing unit configured to receive the reflected light field from the endoscopic probe to reconstruct an image using a ray-optics reconstruction operation. The image processing unit may be configured to employ point-spread function (PSF) calibration in the ray-optics reconstruction operation. The PSF calibration may involve fitting an experimental depth-dependent magnification function M(z) with a ray-optics model of magnification.

A method of operating an optical microscopy system according to principles described herein may include uniformly illuminating an endoscopic probe having a plurality of integrated fiber optics for uniform illumination; capturing a reflected light field, for light-field imaging, through a gradient index (GRIN) lens array, including (i) one or more on-axis sampling of the reflected light field and (ii) two or more off-axis sampling of the reflected light field; and reconstructing an image via a reconstruction algorithm using (i) the one or more on-axis sampling of the reflected light field and (ii) the two or more off-axis sampling of the reflected light field.

The method may include calibrating the reconstruction algorithm using a point-spread function (PSF) that fits an experimental depth-dependent magnification function M(z) with a ray-optics model of magnification.

A non-transitory computer-readable medium may be provided having instructions stored thereon, wherein execution of the instructions by a processor causes the processor to perform any of the methods described herein.

A non-transitory computer-readable medium may be provided having instructions stored thereon, wherein execution of the instructions by a processor causes the processor to perform operations for any of the systems described herein.

In an exemplary embodiment, an optical microendoscopy system may include an endoscopic probe, the probe having a plurality of integrated fiber optics for uniform illumination and an array of gradient index (GRIN) lenses configured to capture a reflected light field from one or more on-axis sampling of the reflected light field and two or more off-axis sampling of the reflected light field. The captured reflected light field may include 6 off-axis samples.

The plurality of integrated fiber optics may include 3 or more fibers embedded within an endoscopic probe core, each having an illumination output.

Each of the fiber optics may include an illumination output at an end of the endoscopic probe, wherein the illumination outputs are distributed equally at the end of the endoscopic probe. The GRIN lens array have 6 GRIN lenses.

The 6 GRIN lenses may be positioned in a hexagonal array at the end of the endoscopic probe. In this aspect, the optical microendoscopy system may include a seventh GRIN lens at a center of the hexagonal array at the end of the endoscopic probe.

The optical microscopy system may further include an illumination output of one of the integrated fiber optics at a center of the hexagonal array at the end of the endoscopic probe.

GRIN lenses of the GRIN lens array may alternate with illumination outputs of individual ones of the integrated fiber optic at an end of the endoscopic probe.

In an aspect, the optical microendoscopy system may further include an image processing unit configured to receive the reflected light field from the endoscopic probe to reconstruct an image using a ray-optics reconstruction operation.

The image processing unit may be configured to employ point-spread function (PSF) calibration in the ray-optics reconstruction operation. The point-spread function (PSF) calibration may involve fitting an experimental depth-dependent magnification function M(z) with a ray-optics model of magnification.

In an aspect, a first subset of the GRIN lenses in the array may comprise a first property and wherein a second subset of the GRIN lenses in the array comprise a second property different from the first. For example, the first property may be a first polarization and the second property may be a second polarization. A third subset of GRIN lenses comprises a third property different from the first property and the second property.

The first property, the second property and the third property may be, for example, polarization, fluorescence in addition to the bright field, wavelength, or time-gated light. The integrated fiber optics may include LED light sources. The endoscopic probe may include a Hopkins rod lens. The endoscopic probe may include a gradient index relay. There may be a laser light source at an end of the endoscopic probe and a camera for receiving reflected laser light. The laser light source may illuminate in a near-infrared range.

A method of operating an optical microendoscopy system according to principles described herein may include providing illumination from the end of an endoscopic probe, the endoscopic probe having a plurality of integrated fiber optic illumination sources for uniform illumination; capturing a reflected light field, for light-field imaging, through an array of gradient index (GRIN) lenses, including (i) one or more on-axis sampling of the reflected light field and (ii) two or more off-axis sampling of the reflected light field; and reconstructing an image via a reconstruction algorithm using (i) the one or more on-axis sampling of the reflected light field and (ii) the two or more off-axis sampling of the reflected light field. The method may also include calibrating the reconstruction algorithm using a point-spread function (PSF) that fits an experimental depth-dependent magnification function M(z) with a ray-optics model of magnification.

The method may also include reconstructing images of a microscopy sample at different z-axis distances from the microscopy sample. Illumination from the end of the endoscopic probe may be provided by a plurality of illumination outputs of the integrated fiber optic light sources in a uniform distribution at the end of the endoscopic probe.

The GRIN lenses of the GRIN lens array may alternate with illumination outputs of individual ones of the integrated fiber optic at an end of the endoscopic probe. The array of GRIN lenses may be a hexagonal array.

The method may include providing a laser light source from the end of the endoscope and performing laser speckle contrast imaging (LSCI) using reflection of light provided by the laser light source. The laser light source may illuminate in a near infrared range. The laser speckle contrast imaging may involve capturing an image of reflected laser light and measuring speckle contrast of different areas of the image of the reflected laser light. The speckle contrast may be a function of pixel illumination and window mean intensity. The LSCI may be performed before reconstructing the image via the reconstruction algorithm, and results of the reconstructing are superimposed on results of the LSCI. Reconstructing the image via the reconstruction algorithm may be performed before the LSCI, and results of the LSCI are superimposed on results of the LSCI.

A non-transitory computer readable medium may be provided having instructions stored thereon, wherein execution of the instructions by a processor causes the processor to perform any method described herein.

A system for processing images in microendoscopy according to principles described herein may include a memory comprising executable instructions and a processor configured to execute the executable instructions and cause the system to perform any method described herein.

While described herein as being directed to an optical microendoscopy system, the probe described herein, separate from the overall optical microendoscopy system, falls within the scope of this disclosure. That is, an endoscopic probe may have a plurality of integrated fiber optics for uniform illumination and an array of gradient index (GRIN) lenses configured to capture a reflected light field from one or more on-axis sampling of the reflected light field and two or more off-axis sampling of the reflected light field. The probe can include all of the configurations described herein. For example, the plurality of integrated fiber optics may include 3 or more fibers embedded within an endoscopic probe core, each having an illumination output. Each of the fiber optics may include an illumination output at an end of the endoscopic probe, wherein the illumination outputs are distributed equally at the end of the endoscopic probe. The GRIN lens array has 6 GRIN lenses. The 6 GRIN lenses may be positioned in a hexagonal array at an end of the endoscopic probe. The probe may include a seventh GRIN lens at a center of the hexagonal array at the end of the endoscopic probe. The optical microscopy system may further include an illumination output of one of the integrated fiber optics at a center of the hexagonal array at the end of the endoscopic probe. GRIN lenses of the GRIN lens array may alternate with illumination outputs of individual ones of the integrated fiber optic at an end of the endoscopic probe.

It should be noted that the number of GRIN lenses can be reduced, perhaps at the cost of some resolution, without departing from the spirit and scope of the principles described herein. For example, 3, 4, 5, 6, or 7 GRIN lenses can be used as long as there is sufficient angular information to reconstruct a 3D image as described herein. It is also possible to replace some of the GRIN lenses with a light source. For example, in one configuration, 6 GRIN lenses are provided in a hexagonal configuration with a light source at the center. Additional or alternate light sources can be provided at a predetermined pitch on the end of the endoscopic probe to provide uniform or known illumination.

Example System

FIG. 1 shows a GRIN lens array microendoscopy (GLAM) design and image formation according to the principles described herein. FIG. 1(*a*) is a CAD model of the endoscope assembly. FIG. 1(*b*) shows an assembled endoscope system with overlaid dimensions of the insertion tube. The inset shows a close-up of the 3D-printed core of the insertion tube that holds the seven GRIN lenses and six illumination fibers. FIG. 1(*c*) is a schematic diagram of light propagation through the system. RL, doublet relay lenses.

The prototype included a hexagonal GRIN lens array (GLA) developed to harness the benefits of light-field over stereoscopic imaging while mitigating the imaging quality trade-offs induced with conventional light-field methods (FIG. 1). Due to their optical properties, GRIN lenses can maintain a high numerical aperture (NA) within a physically confined space, allowing for dense 2D spatial sampling [29]. In the study, previous optical proof of concept of GRIN lens array imaging [30] is incorporated into a handheld, compact, full-color realization with integrated illumination. Using 1-mm diameter GRIN lenses, the system can acquire 2D angular information at a pitch of 1.4 mm, keeping the entire probe diameter under 5 mm, consistent with 3D endoscopes currently used in the clinic (FIG. 1(*a*)). In this sense, one 2D camera frame, consisting of seven angular elemental samples, one on-axis, and six off-axis, permits a dense sampling of the light field to produce a quantitative 3D reconstruction. The GLAM prototype also contains six integrated optical fibers between the GRIN lenses for onboard illumination (FIGS. 1(*a*) and (*b*)). Other configurations of optical fibers may be employed to provide uniform illumination, e.g., 2, 3, 4, 5, 6, 7, 8, 9, 10, 11, 12, 13, 14, 15, 16, 17, 18, 19, 20, 20+. Additionally, the system can be integrated for full-color acquisition, gaining a more natural vision for better practicality (FIGS. 1(*a*) and (*b*)).

Figure 2:
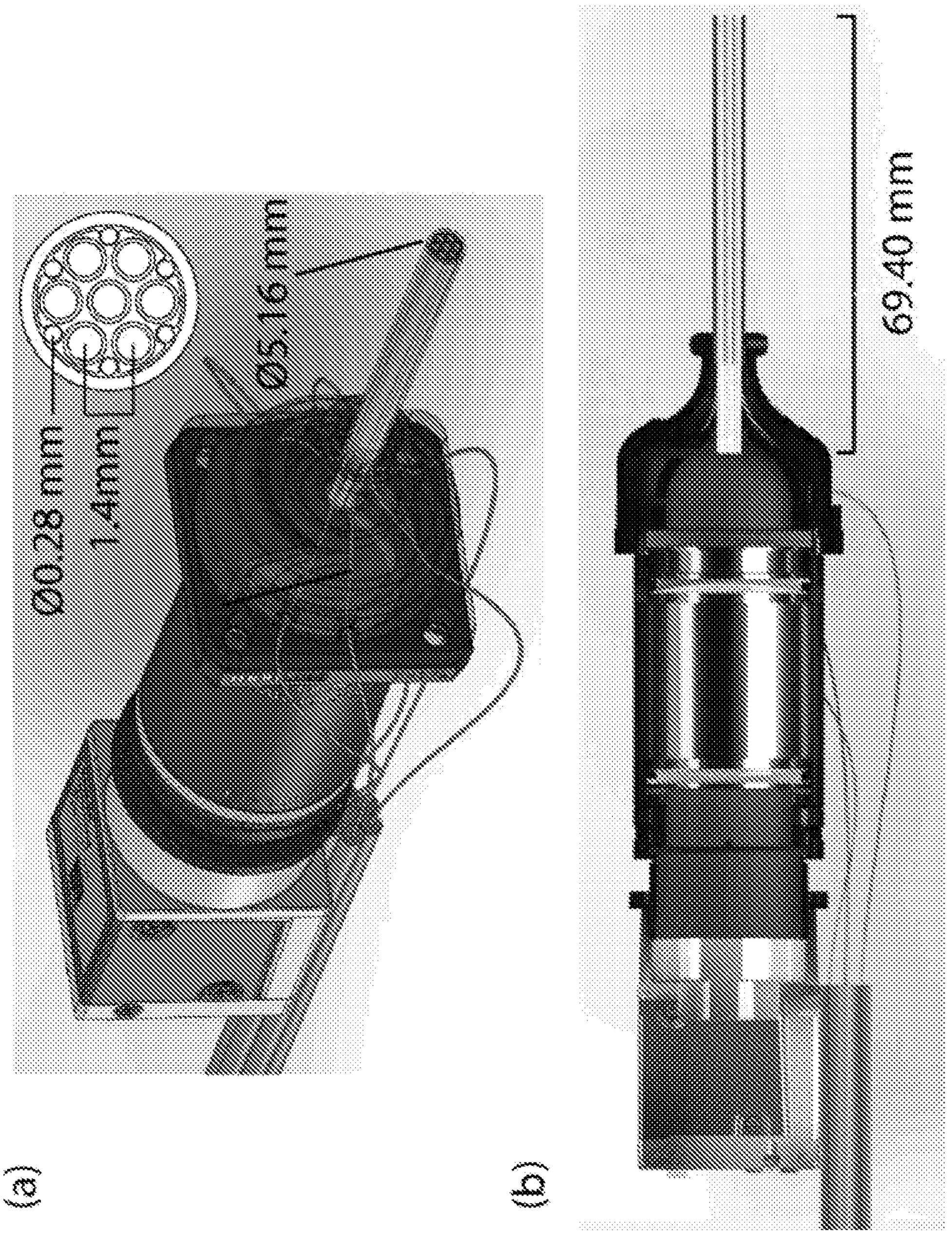
FIG. 2(*a*) is a transparent rendering of a GLAM according to principles described herein.

FIG. 2(*a*) is a transparent rendering of a GLAM according to principles described herein; FIG. 2(*b*) is a cutaway rendering of a GLAM according to the principles described herein. FIG. 2(*a*) shows a CAD model of the GLAM showing fiber implementation into the imaging probes. Each fiber is individually threaded into the imaging probe. FIG. 2(*b*) shows a cutaway view of the GLAM system showing the GRIN lens extension past the fiber entry point followed by two achromatic doublets and the CMOS RGB camera.

In some embodiments, GLAM can be constructed from a combination of off-the-shelf components and custom 3D-printed parts. All custom parts were designed in SOLIDWORKS® and printed with a resin 3D printer (Form 2, FLGPBK023D, Formlabs). The GLAM imaging probe is composed of an inner 3D printed core that houses seven 1-mm diameter 0.5NA GRIN lens assemblies (GRINTECH, GT-ERLS-100-005-150) arranged with a pitch of 1.4 mm hexagonally within individual tubes. Illumination is provided by an LED source (Thorlabs, MWWHF2), and the outside of the core has six grooves for threading optical fibers (Thorlabs, BF72HS01) between the inner core and outer sheath. The outer sheath is a 304 Stainless Steel Tube (McMaster-Carr, 8987K7) with an outer diameter of 0.203" (5.15 mm) and a wall thickness of 0.01" (0.25 mm). The probe fits into a custom holder with a side access door to align the lenses (FIGS. 1 and 2). The fibers were threaded through isolated channels in the holder, beyond which the coated GRIN lenses were extended to relay the image without significant interference from the light leakage. The image is relayed by an achromatic lens pair (Thorlabs, mAP103040-A) to a color camera (Basler Ace 304 acA1920-25uc).

Example Algorithm

The system may utilize a ray-optics reconstruction without any computationally costly deconvolution to reduce the computational burden for eventual clinical application. This approach can enable full-color quantitative reconstruction of spatially dense samples over centimeters of depth while reducing reconstruction time by an order of magnitude over the previous wave-optics model. The reconstruction procedure is based on the optical parametrization outlined in FIG. 1(*c*). Each lens samples a differently angled cone of light rays reflected from each point on the object. The object space coordinates are denoted as ($x_o$, $y_o$, $z_o$), and the image space coordinates are denoted as ($x_\xi$, $y_\xi$). GRIN lenses are spaced with a pitch of $\alpha_o$ in object space and correspondingly, a in the image space. The ray optics formulation of the light-field reconstruction can be derived as a shearing process in 3D space. For GLAM, the mapping of the object space to the image space over an axial depth z is given by the depth-dependent magnification function M(z). By pre-calibrating the magnification M(z) of the system, each layer of the 3D reconstruction can be encoded with a quantitative depth.

System Calibration

A detailed discussion of the point-spread function (PSF) calibration can be found below. The latest version of the software will be available upon publication at: https://github.com/ShuJiaLab/3D_endoscopy.

Figure 3:
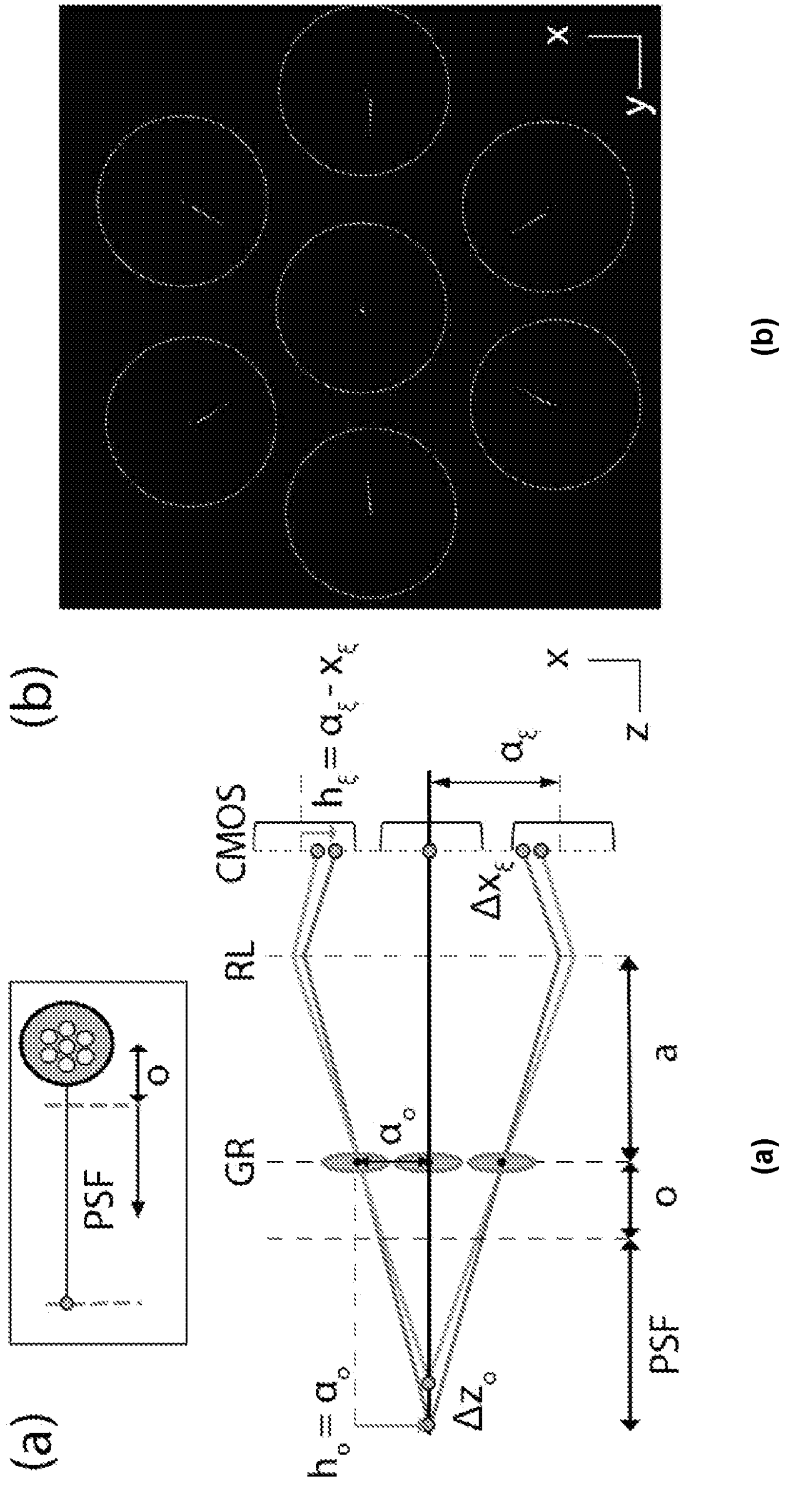
FIGS. 3(*a*)-(*b*) provide a magnification model according to the principles described herein.

FIG. 3 provides a magnification model according to the principles described herein. FIG. 3(*a*) shows two different positions of the pinhole represented by the green dot. With each axial shift, $\Delta z_o$ is encoded in the PSF with a lateral shift $\Delta x_\varepsilon$. GR is the GRIN/relay system, RL is the achromatic doublet relay lens pair. The two variables O and a represent the offsets of the PSF region from the system and the GRIN-to-relay spacing, respectively. FIG. 3(*b*) shows an x-y projection of the PSF volume, showing the cumulative shifts in the pinhole image in the off-axis lenses proportional to the magnification of the system. FIG. 3(*c*)

A light-field system maps axial shifts in the object space to lateral shifts in the image space—thus encoding the depth into 2D information. The reconstruction process is an inverse mapping, i.e., a back projection. As a pre-calibration step for reconstruction, the PSF of the system is acquired as depicted schematically in the box within FIG. 3(*a*). First, a pinhole is aligned on the optical axis of the center lens and placed as close as possible to the system—displaced by an arbitrary offset O. Light from the pinhole passes first through each of the seven lenses, six of them offset from the center lens by a pitch $\alpha_0$, and then through the achromatic lens pair to form the final image on the camera. The distance from the relay to the camera is a set parameter in our system, while the distance from each GRIN relay to the relay lens pair is tunable during alignment, thus represented by the distance variable a. The final magnification of the pinhole image can be seen in this case as $$M = \frac{h_\xi}{h_o} = \frac{(x_\xi - \alpha_\xi)}{\alpha_o}.$$

As the pinhole is translated in steps of $\Delta z_0$=50 μm, there is a corresponding shift in image space given by $\Delta x_\varepsilon$. The shift $\Delta x_\varepsilon$ is proportional to the magnification change of the system over $$\Delta z_o,\ M(\Delta z_o) = \frac{h_\xi}{h_o} = \frac{(\Delta x_\varepsilon - \alpha_\xi)}{\alpha_o}.$$

FIG. 3(*b*) shows a cumulative z projection of the entire PSF volume. Though the pinhole remains on the optical axis in the center lens, and thus $h_o$ is not changing, it can be seen that $x_\varepsilon$ has changed for every axial shift according to the depth-dependent magnification of the system M(z).

Figure 5:
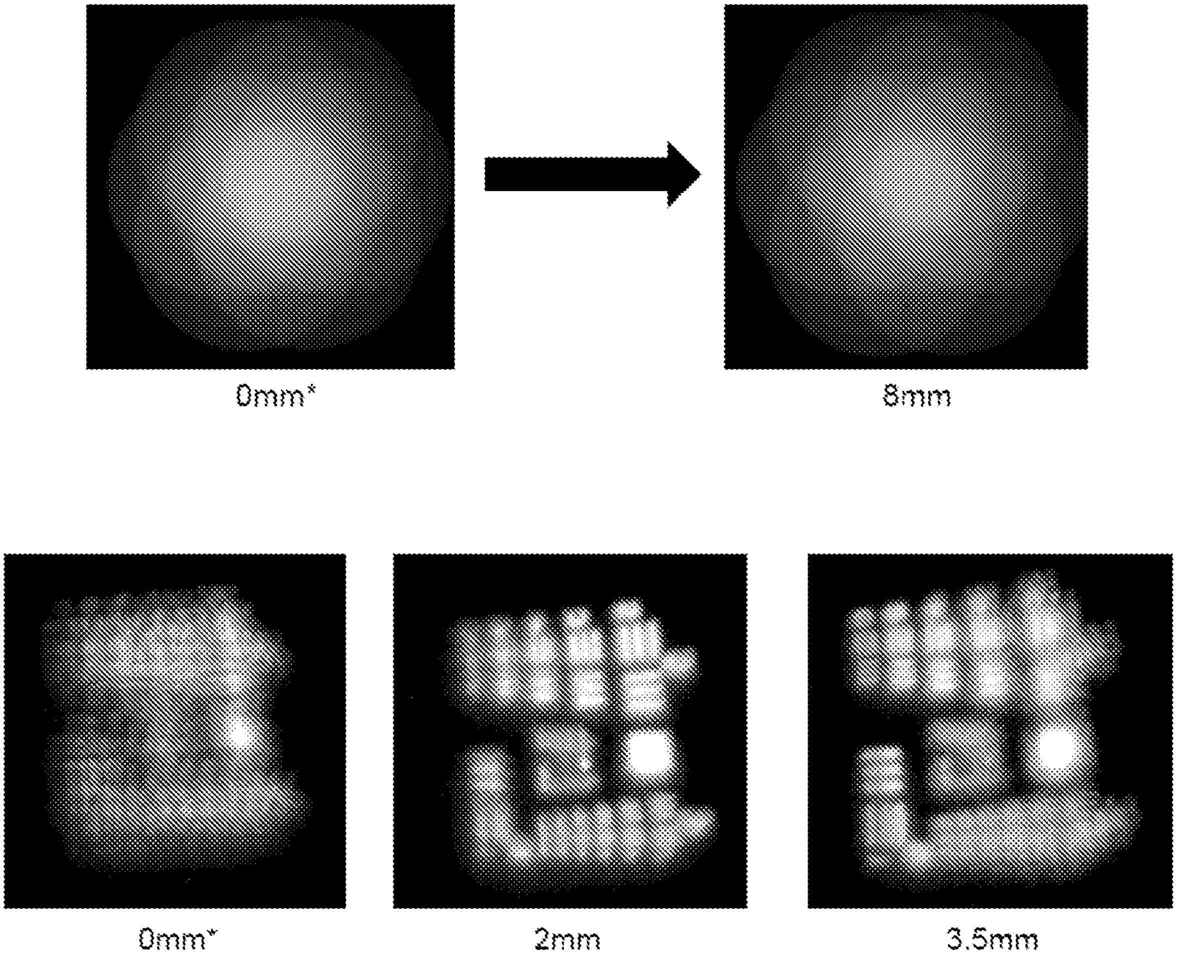
FIG. 5 provides example images showing shift compensation according to an embodiment of the present disclosure.
Figure 6A:
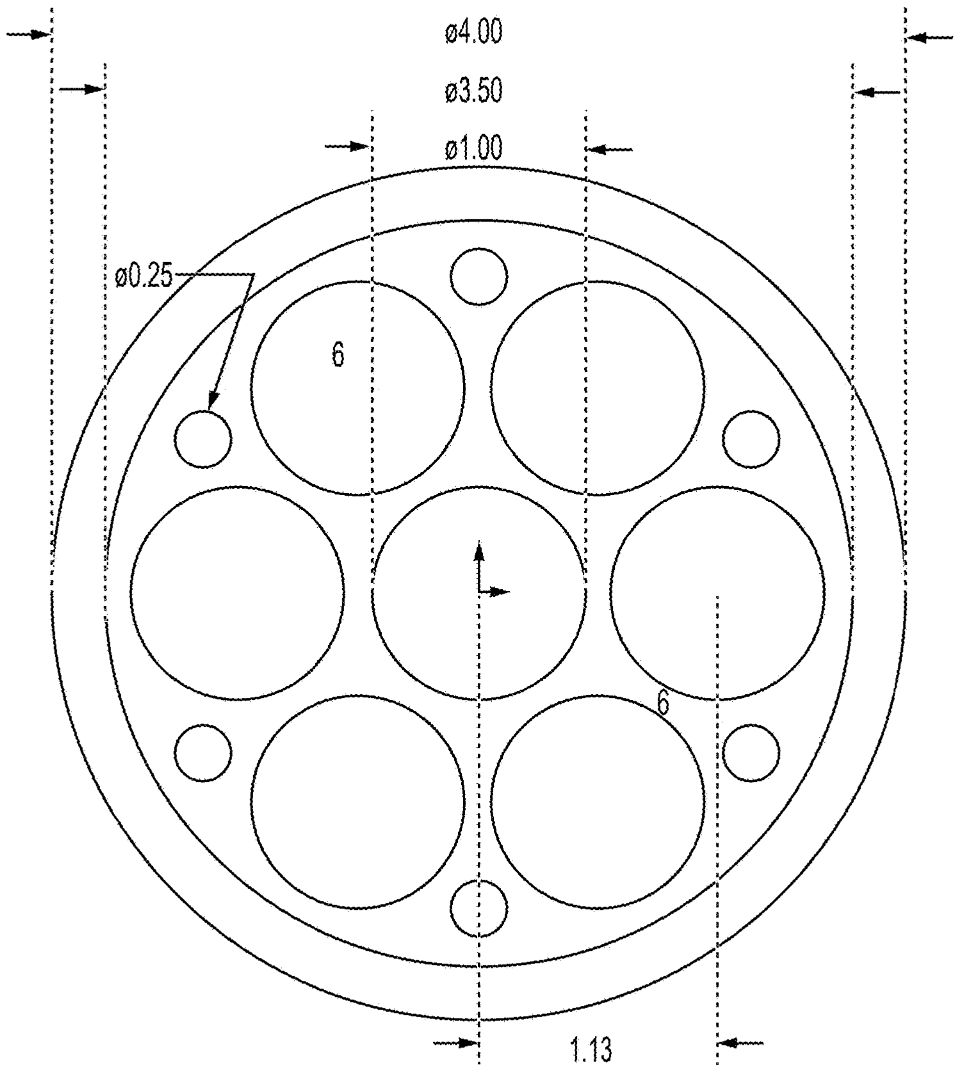
FIG. 6(*a*) shows an example nanoscribe GRIN lens configuration according to the principles described herein.
Figure 6B:
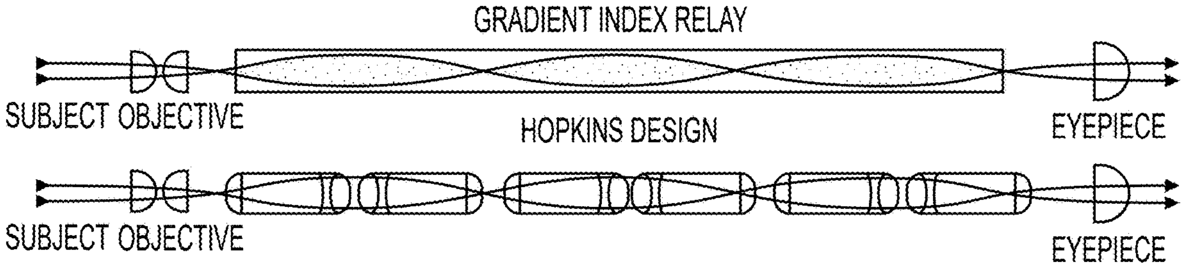

As illustrated by FIGS. 4(*a*) and 4(*b*), by characterizing the point spread function to determine the amount of lateral shift per increment z, the shift can be compensated to bring different views into focus. FIG. 5 is an example image showing shift compensation according to an embodiment of the present disclosure. FIG. 6(*a*) shows an example nanoscribe GRIN lens configuration according to the principles described herein. The nanoscribe GRIN lens configuration shown in FIG. 6(*b*) may be used with a GRIN lens relay, such as a Gradient Index Relay or a Hopkins Rod.

Figure 7:
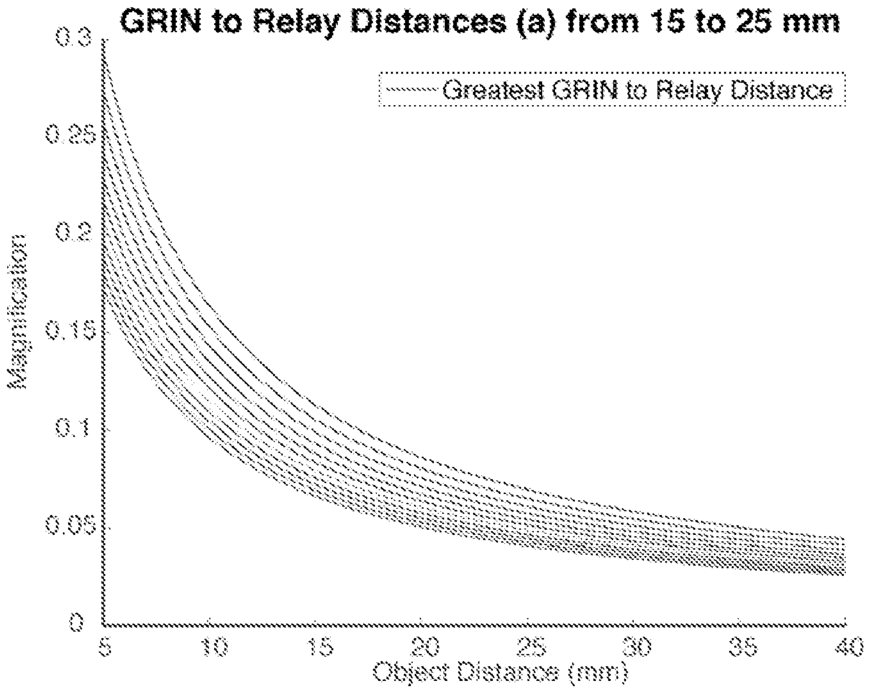
FIG. 7 shows ray-optics simulations of M(z), including simulations of changing GRIN-to-relay distance over a 40-mm axial distance.

FIG. 7 shows ray-optics simulations of M(z), including simulations of changing GRIN-to-relay distance over a 40-mm axial distance. The farther the lenses are from each other, the more gradual the magnification decrease will be. This corresponds to a larger FOV but lowers the axial and lateral resolution. A changing O parameter can be conceptualized as shifting this graph left or right for different offsets.

To fully characterize the mapping from the object to image space, we further solved for the unknowns offset O and GRIN-to-relay spacing a. This is achieved by fitting the experimental M(z) with a ray-optics model of magnification in our system. Changing the GRIN-to-relay spacing will alter the magnitude of M(z), while different PSF offsets will left- or right-shift the portion of the curve captured by our PSF. FIG. 7 shows example M(z) functions with different GRIN to relay spacing. The experimental magnification data is fit to this model to simultaneously solve for both a and O.

Experimental Results and Examples

Chromatic Characterization

Figure 8:
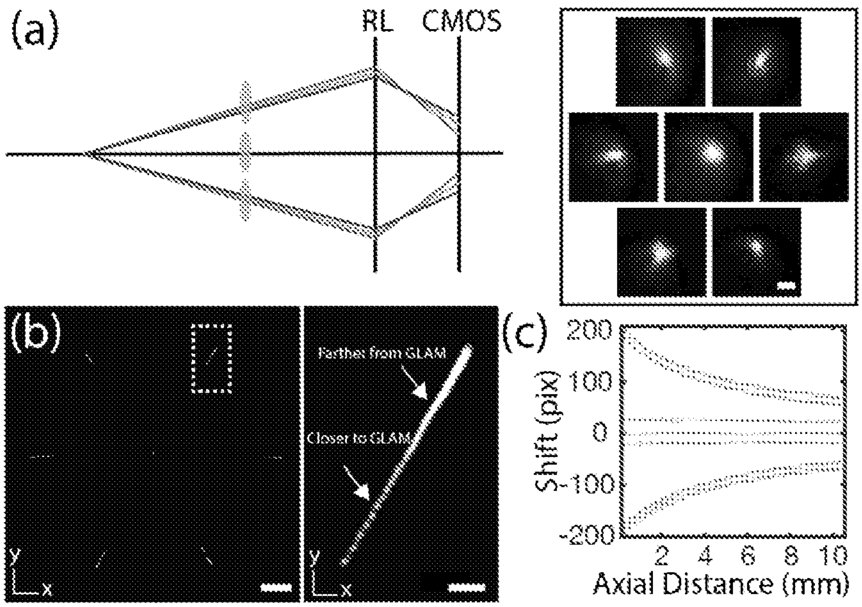
FIG. 8(*a*) shows the schematic depiction of the RGB acquisition and one axial plane of the resulting RGB PSF.

GLAM is calibrated through the acquisition of the PSF of the system. A pinhole is aligned along the optical axis of the center GRIN lens and translated axially. FIG. 8(*a*) shows the schematic depiction of the RGB acquisition and one axial plane of the resulting RGB PSF. Chromatically dependent displacement can be observed in the six off-axis GRIN lenses, with longer wavelengths tending towards the center of the GLA and shorter wavelengths shifting outward from the center. As the off-axis lenses capture angular information of the pinhole on the central optical axis, this displacement is a direct measurement of the axial chromatic effect in the system, an aberration common to GRIN lenses. As the pinhole is translated towards the system, the chromatic shifts change as a function of the magnification, as shown in FIG. 8(*b*), displaying an x-y projection of the entire 3D PSF over an axial range of 22 mm. It can be seen that the RGB pinhole images are more spread apart when the pinhole is close to the system and gradually come closer together as it moved away. The corresponding pixel shifts are quantified as in FIG. 8(*c*), where the shift value is projected along the y-z axis. With the ray-optics model described herein, we determine the axial offset between the RGB channel images to be ~36 μm, reasonably close to the nominal value of ~24 μm provided by the manufacturer for the GRIN-relay system alone.

FIG. 8 shows a chromatic calibration of GLAM. FIG. 8(*a*) shows a schematic representation of axial chromatic aberration in the system. The inset shows laterally displaced RGB PSF positions in the off-axis elemental images. FIG. 8(*b*) shows an axial stack projection (step size=50 μm) of the RGB PSF within an axial range of 22 mm. The inset shows the zoomed-in image of the yellow-boxed region. The colors can be clearly resolved closer to GLAM, indicating an enhanced axial resolution. FIG. 8(*c*) shows a projection of the PSF shift from lens center for each elemental image along the y-z axis. A 0-10 mm axial displacement range is shown for better visualization of the point separation close to the endoscope. Scale bars: 20 μm (FIG. 8(*a*)), 500 μm (FIG. 8(*b*)), 50 μm (FIG. 8(*b*), inset).

Theoretical Resolution and Field of View

Figure 9:
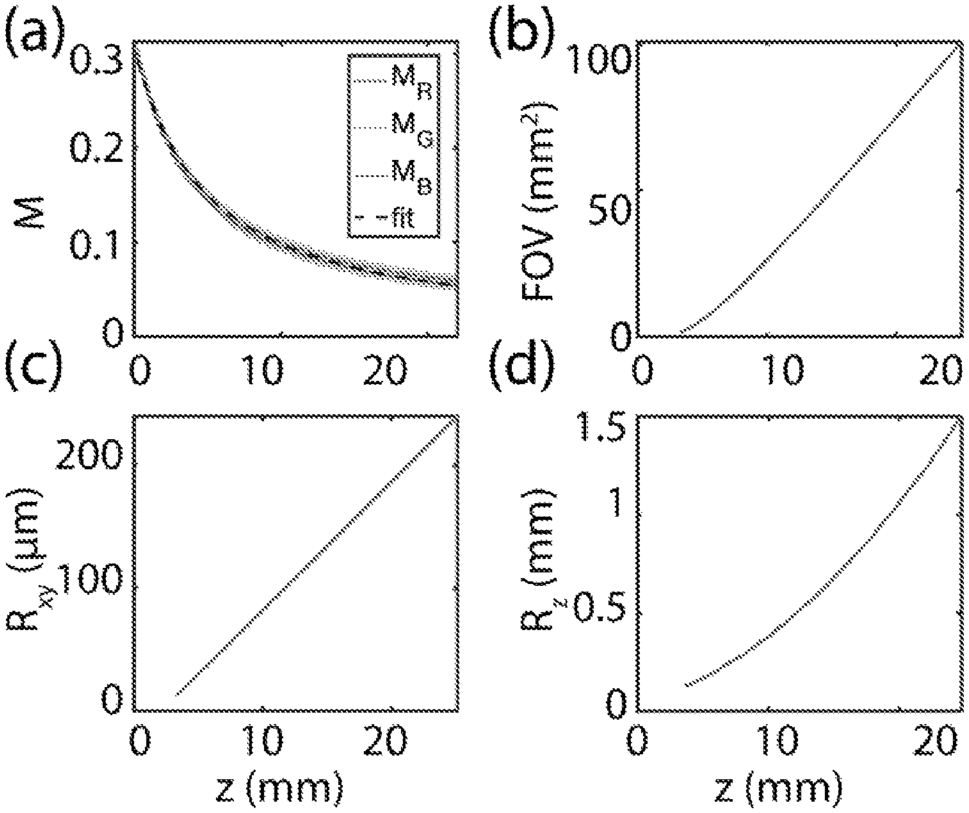
FIGS. 9(*a*)-(*d*) shows system characterization using M(z).

FIG. 9 shows system characterization using M(z). FIG. 9(*a*) is shows that the magnification of RGB is a function of the distance of the object from the system. The solid lines show the average magnification for each color, and the shaded areas represent the standard deviation over all the lenses. FIG. 9(*b*) shows the field of view (FOV), defined as the overlapping region of all seven lenses in the reconstruction. FIG. 9(*c*) shows the Nyquist sampling resolution limit of the system. FIG. 9(*d*) shows axial resolution given as the smallest resolvable axial shift over distance.

The RGB magnification curves were averaged prior to fitting the model to determine the average pinhole position, shown in FIG. 9(*a*). The magnification function of the system determines the pixel size of the image space, which sets the upper limit on the field of view (FOV) and sampling resolution (FIG. 9(*b*) and FIG. 9(*c*)). The FOV is a function of axial distance and is defined here as the area where all seven lenses contribute intensity information within each reconstructed axial plane. Such an area exhibits the highest SNR for the final image, though regions outside this FOV can still contribute to the reconstruction. Individual RGB lens M(z) data and experimental measurements of the FOV are shown below. With our model, the sampling resolution remains under 250 μm, and the FOV can achieve 1 $cm^2$ at 20 mm away from the system (FIG. 9(*b*) and FIG. 9(*c*). The sampling resolution becomes worse due to the effects of diffraction and aberrations present in the system. The axial resolution limit of GLAM can be conceptualized in opaque samples as the smallest axial shift that translates to a measurable lateral shift on the camera. FIG. 9(*d*) shows the theoretical limit for axial translations or topological features that can be resolved with GLAM.

System Alignment and Characterization

Figure 10:
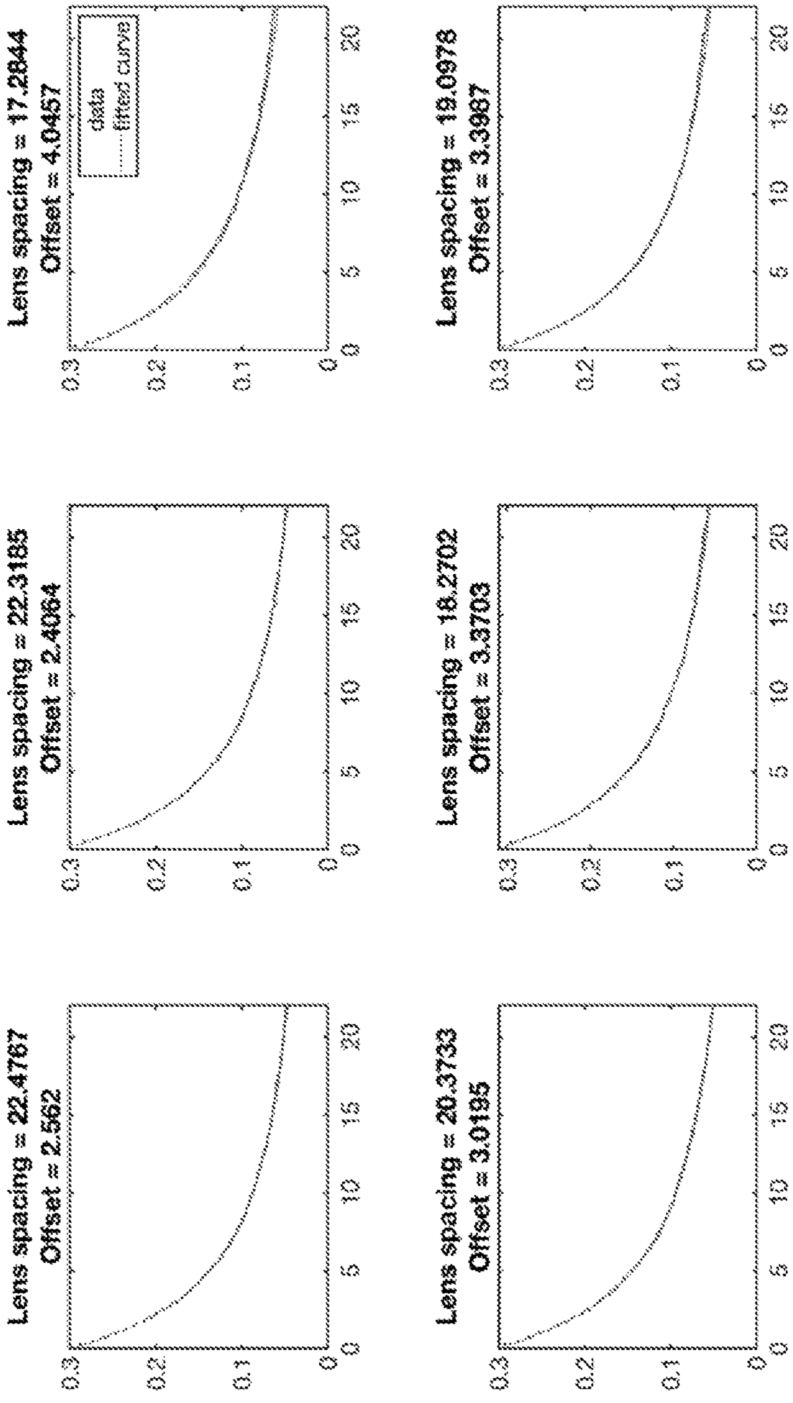
FIG. 10 shows the magnification function M(z) per lens.

Each of the seven GRIN lenses in GLAM is separately aligned until its image sharpness reaches a maximum. Characterization of the lens-by-lens alignment of the off-axis lenses can be seen in FIG. 10. FIG. 10 shows the magnification function M(z) per lens. Magnification fits for each of the seven lenses in a single channel. There are slight shifts in the lenses representing misalignments in the system. An extra iterative calibration step could be added to pre-calibration to minimize the difference in these fits before imaging.

Figure 11:
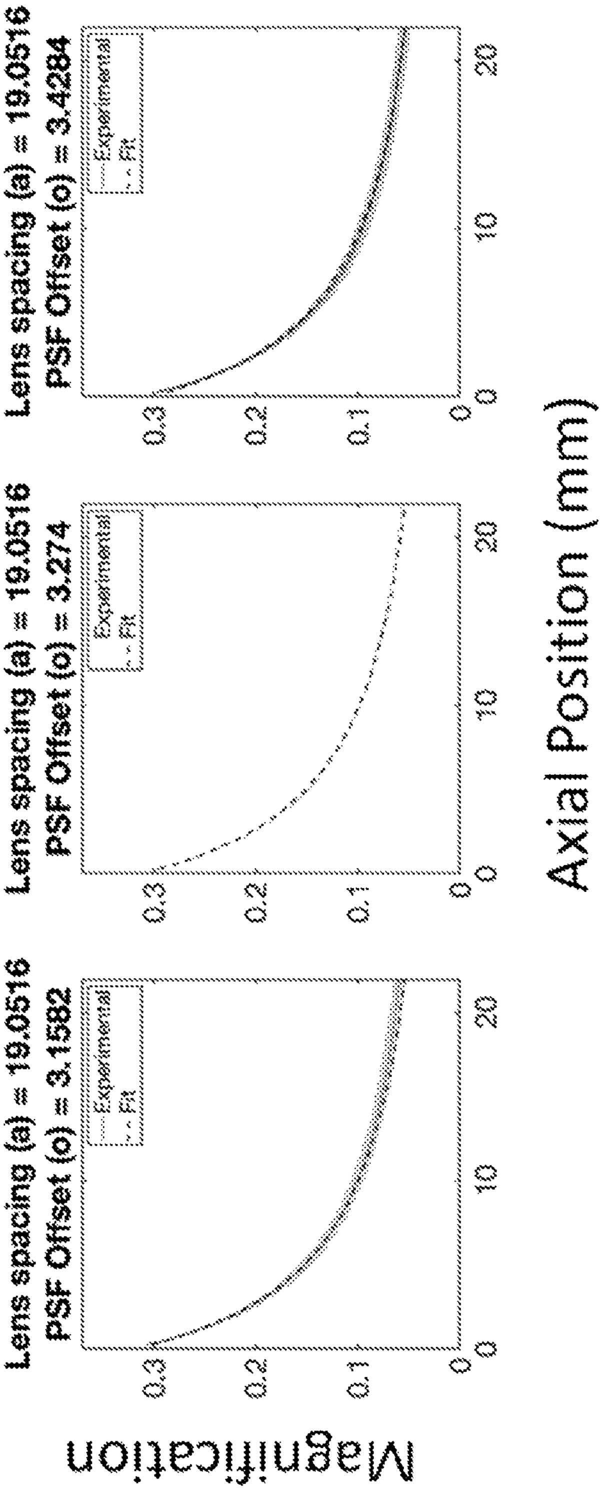
FIG. 11 shows RGB M(z) with fixed lens spacing (a).

FIG. 11 shows RGB M(z) with fixed lens spacing (a). As the RGB PSF is acquired for all the colors simultaneously, parameter (a) should not change between channels. The thick line shows the bounds of the individual lens fits, whose average is the solid line. The dotted line represents the fit to the theoretical model. When a is fixed, we can see the shifts in offset caused by axial chromatic aberrations in the system.

The six M(z) functions are averaged in each RGB channel, as shown in FIG. 11. Finally, the color channels are averaged to produce the cumulative multi-color magnification function shown in FIG. 9(*a*). The theoretical lateral and axial resolution limits are shown in FIGS. 9(*a*)-(*d*) are then derived from the average curve. The Nyquist sampling resolution limit for lateral resolution is given at each axial position by $R_{xy}=2(M(z)\times S_{pixel})$, where $S_{pixel}$ is the physical size of the camera pixel. The axial resolution of the system can be thought of as the smallest axial shift that will result in an observable lateral shift on the camera. This is calculated by finding the size of the axial shift around a given reference z position that results in a lateral shift greater than the lateral resolution limit on the camera $2(M(z\pm\Delta z)\times S_{pixel})>R_{xy}$.

Figure 12:
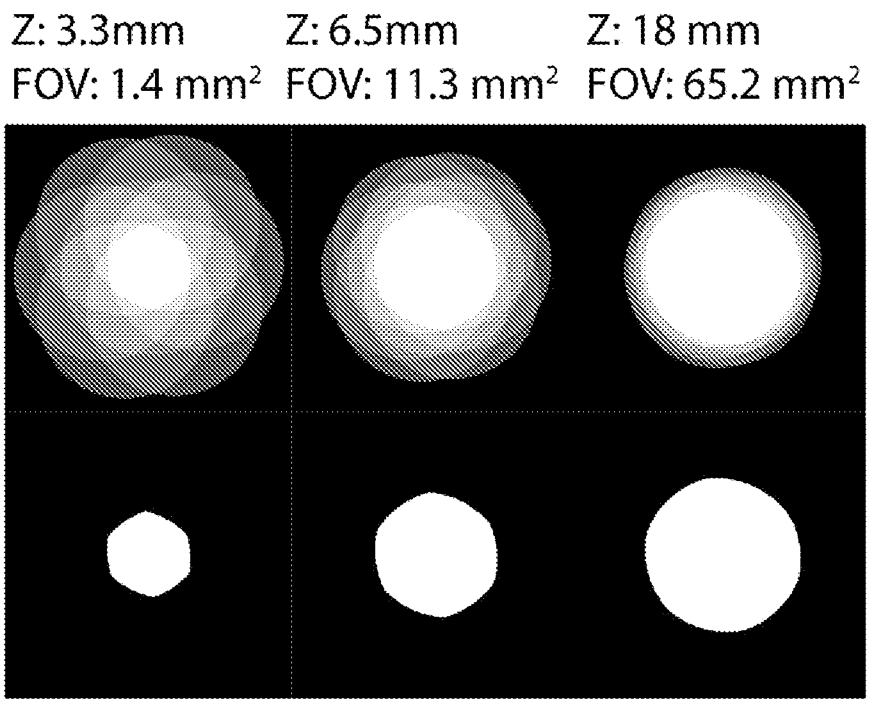
FIG. 12 shows FOV images for three distances from the GLAM system.

The effective field of view of GLAM will change over the imaging depth depending on the overlap in the viewing region of each lens as well as the changing effective pixel size (see FIG. 9(*b*)). FIG. 12 illustrates FOV calibration. FIG. 12 shows FOV images for three distances from the GLAM system. Closer to the system, there is less overlap from the off-axis lenses, reducing the FOV. Farther away from the system, the overlap and pixel size increase, resulting in an increased FOV. The field of view of GLAM was calibrated by reconstructing a binary mask of the GLA. The top row shows the FOV with all seven lenses, and the bottom region shows the area where their viewing regions overlap. The latter was considered the FOV, though other regions can contribute lower SNR information to the reconstruction.

Characterization of Lateral Resolution

Figure 13:
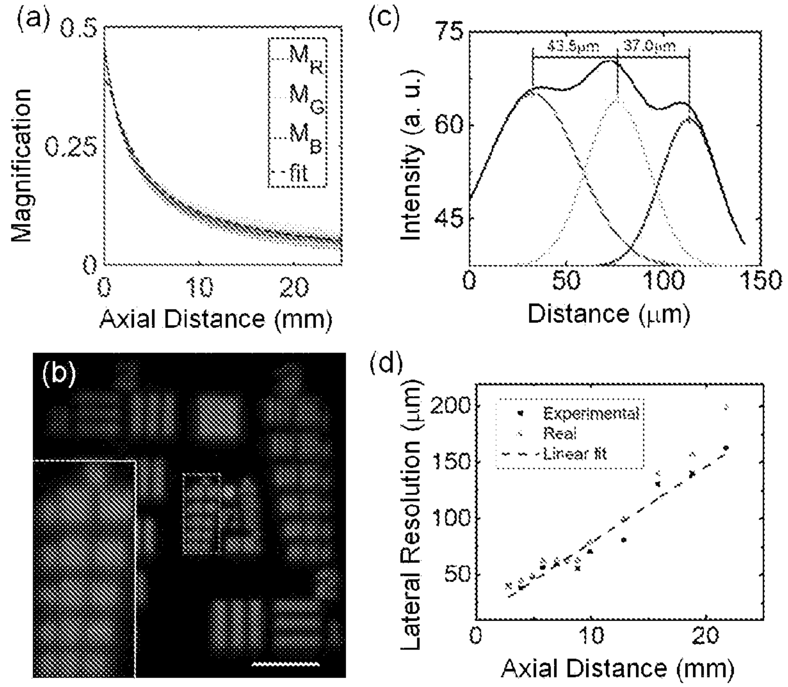
FIGS. 13(*a*)-(*d*) illustrate experimental system characterization.

FIG. 13 illustrates experimental system characterization. FIG. 13(*a*) shows the magnification of RGB as a function of distance from the system. Solid lines show the average magnification for each color, and the shaded areas represent the standard deviation over all the lenses. FIG. 13(*b*) shows reconstructed RGB images of the USAF target taken at 2.85 mm away from GLAM. The inset shows the zoomed-in image of Group 4 (physical size: 535 m×1173 m). In FIG. 13(*c*), the black curve shows the overall intensity profile along the finest resolvable elements indicated by the red line in FIG. 13(*b*). The red, green, and blue curves represent the Gaussian fitting of the three corresponding bars. FIG. 13(*d*) shows measurements of the experimental lateral resolution obtained for RGB data as a function of distance from GLAM. The magenta points represent the real distance between the bars as a function of distance from GLAM, and the dashed line represents the line of best fit for the data. Scale bar: 1 mm. Experimentally, the axially-dependent magnification of the system within a range of 0-22 mm from the endoscope was determined using the PSF (FIG. 13(*a*)).

The magnification can also be used to calculate the effective image pixel size at different depths, which were used to estimate the resolution of the system. To quantify the lateral resolution of GLAM, we mounted and imaged a USAF resolution target (R1DS1N, Thorlabs) on a motorized linear translation stage. These images of the target were taken using transmitted light. FIG. 13(*b*) shows a fused image of the RGB intensity values recorded from 2.85 mm away, and the red line indicates element 5 of group 4 on the target as the finest resolvable element. The intensity graph along the red line is shown in FIG. 13(*c*), where the three bars of the element were identified using Gaussian fitting. The distance between peaks was used to estimate the resolution at that depth, and the data for fused RGB images at all measured depths are shown in FIG. 13(*d*). The lateral resolution exhibits a linear trend, extending from 38 μm to 162 μm across a depth range of 1.85-21.75 mm away from the endoscope, consistent with the predicted results in FIG. 9(*c*). Due to chromatic aberration, the actual distances between element bars of the USAF target group are slightly larger than the experimental values. The detailed data for characterizing the lateral resolution for each color can be found below.

RGB Lateral Resolution

Figure 14:
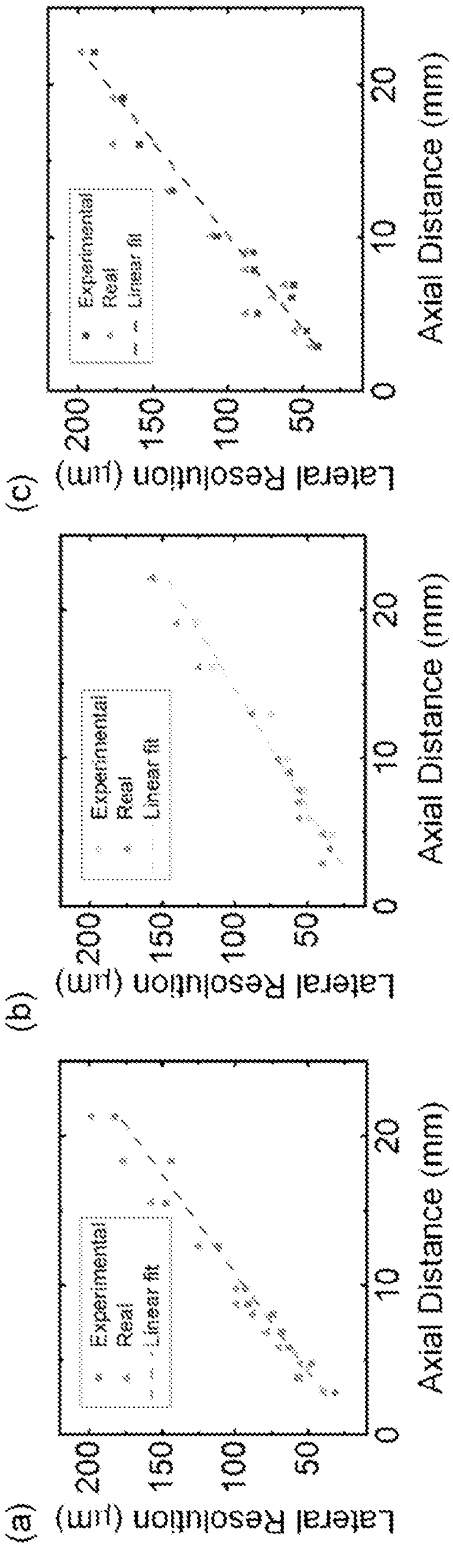
FIGS. 14(*a*)-(*c*) shows measurements of the experimental lateral resolution obtained for red, green, and blue intensity data as a function of distance from the system.

FIG. 14 shows measurements of the experimental lateral resolution obtained for red (FIG. 14(*a*)), green (FIG. 14(*b*)), and blue (FIG. 14(*c*)) intensity data as a function of distance from the system. The magenta points represent the real distance between the bars of the USAF target as a function of distance from the system, and the dashed lines represent the line of best fit for their respective data sets.

Characterization of Axial Resolution

The axial resolution of the system was measured using the same USAF resolution target and transmitted light. The USAF target was mounted on a rotating stage, allowing imaging of the target at a range of angles. Angling the target introduced a variable deviation in the axial position of the bars on the target that was used to determine the smallest axial distance that the system could resolve. The target was imaged at 0°, 10°, 20°, 30°, 40°, and 450 angles.

Figure 15:
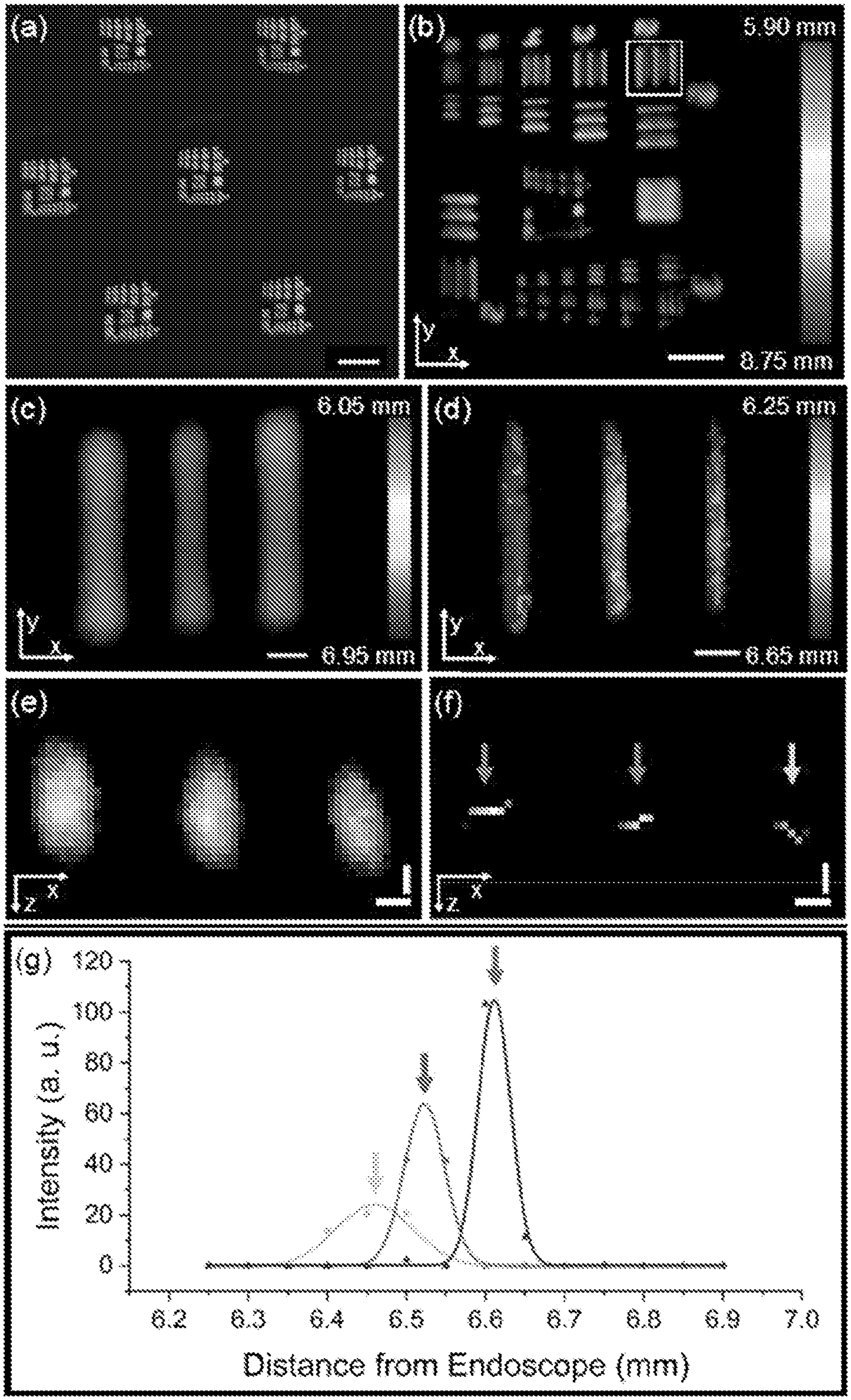
FIGS. 15(*a*)-(*g*) shows axial resolution measurements.

FIG. 15 shows axial resolution measurements. FIG. 15(*a*) is a raw, full-color endoscope image of a USAF resolution target angled at 20°. FIGS. 15(*b*)-(*d*) are full-color reconstructions with true color overlaid with a color gradient to show depth. FIG. 15(*b*) is a full-color reconstruction of the angled USAF target. FIG. 15(*c*) is a full-color reconstruction of the (2, 2) bars indicated by the white box in FIG. 15(*b*). FIG. 15(*d*) is a reconstruction of the (2, 2) set of bars after isolating the weighted maximum intensity, exhibiting the clear depth gradient. FIG. 15(*e*) is a projected top view of the reconstruction in FIG. 15(*c*). FIG. 15(*f*) is a projected top view of the reconstruction in FIG. 15(*d*). FIG. 15(*g*) shows the intensity profiles of the projected bars in FIG. 15(*f*). Gaussian fitting gives centers of the intensity profile of each bar at 6.460 mm, 6.523 mm, and 6.611 mm from the tip of the endoscope, showing a resolved 88-μm distance between the bars with centers at 6.523 mm and 6.611 mm. Scale bars: 500 μm (FIG. 15(*a*)), 750 μm (FIG. 15(*b*)), 100 μm (FIGS. 15(*c*) and (*d*)), 50 μm (FIGS. 15(*e*) and (*f*), vertical), 200 μm (FIGS. 15(*e*) and (*f*), horizontal).

The distance between the target and the endoscope was such that the middle bar of the (2,2) group on the USAF target was 6.5 mm from the endoscope when the target was angled at 200 (FIG. 12). At each target angle, as shown in FIG. 12(*a*), the raw image was used to generate the full-color reconstructions shown in FIG. 5*b*, which were color-coded according to the depth due to the angling of the target. The reconstructions were then processed by isolating the weighted maximum intensity of each pixel throughout the reconstruction stack to remove out-of-focus information in the z-axis (FIG. 12(*c*)-(*f*)). The intensity profile of the bars in the z-axis of the top-view projection (x-z projection) was each fit to a Gaussian distribution (FIG. 12(*g*)). We measured that the system is able to resolve the axial distance between the two Gaussian curves separated by 88 μm, consistent with the theoretical distance of 76 m for the adjacent bars on the USAF target angled at 20°.

Phantom Curvature Estimation

Figure 16:
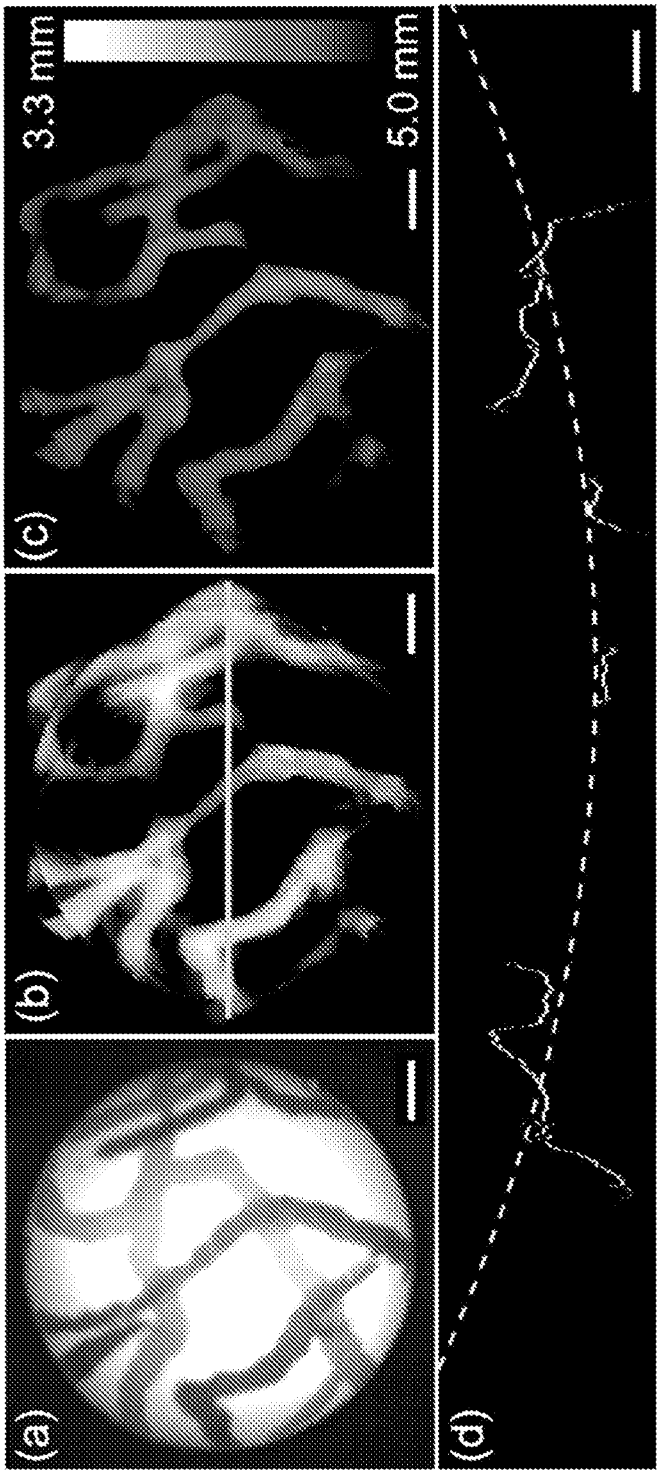
FIGS. 16(*a*)-(*d*) show an imaging phantom curvature.

FIG. 16 shows the imaging phantom curvature. FIG. 16(*a*) shows a raw image from the center endoscope lens of phantom blood vessels wrapped around a 0.5-inch diameter cylinder. FIG. 16(*b*) is a full-color reconstruction of the phantom target, shown in an inverted grayscale image. The weighted maximum of each pixel in the reconstruction stack was extracted, and the resulting stack slices were projected into a single plane. FIG. 16(*c*) shows a depth-coded reconstruction in FIG. 16(*b*) with distance from the endoscope shown by a color gradient. FIG. 16(*d*) is a projected top view of the reconstruction stack along the yellow line in FIG. 16(*b*). The profile was fitted with a dashed circle with a diameter of 0.546 inches. Scale bars: 1 mm (FIGS. 16(*a*)-(*c*)). 500 μm (FIG. 16(*d*)). Next, to further assess the depth estimation ability of the GLAM system, we imaged a phantom target resembling red and blue blood vessels that were wrapped around a half-inch diameter tube.

FIG. 16(*a*) depicts the raw image of the target through the center GRIN lens of the endoscope. A color reconstruction was made from the data. The reconstruction was then converted to the grayscale intensity, and the intensities were inverted to aid in processing. For each pixel, a plane of focus was determined using the intensity and a weighted maximum approach. The planes of focus ranged between 3.04 mm and 5.99 mm away from the endoscope. FIG. 16(*b*) shows a projection of all stack slices into a single plane. FIG. 13(*c*) displays the reconstruction with a color gradient to represent the depth of the plane of focus for each pixel, consistent with the expected depth estimation where the center of the phantom target is closer to the endoscope compared to the outer edges of the target. FIG. 16(*d*) shows a top-down view projection of the reconstruction in FIG. 16(*b*) along the yellow line. The sections of pixels that had a more horizontal trend were used to fit a circle to estimate the surface curvature of the target. The curvature rendered a 0.546-inch diameter, consistent with the actual 0.5-inch diameter of the cylinder.

Quantitative 3D Reconstruction of a Phantom Heart

Figure 17:
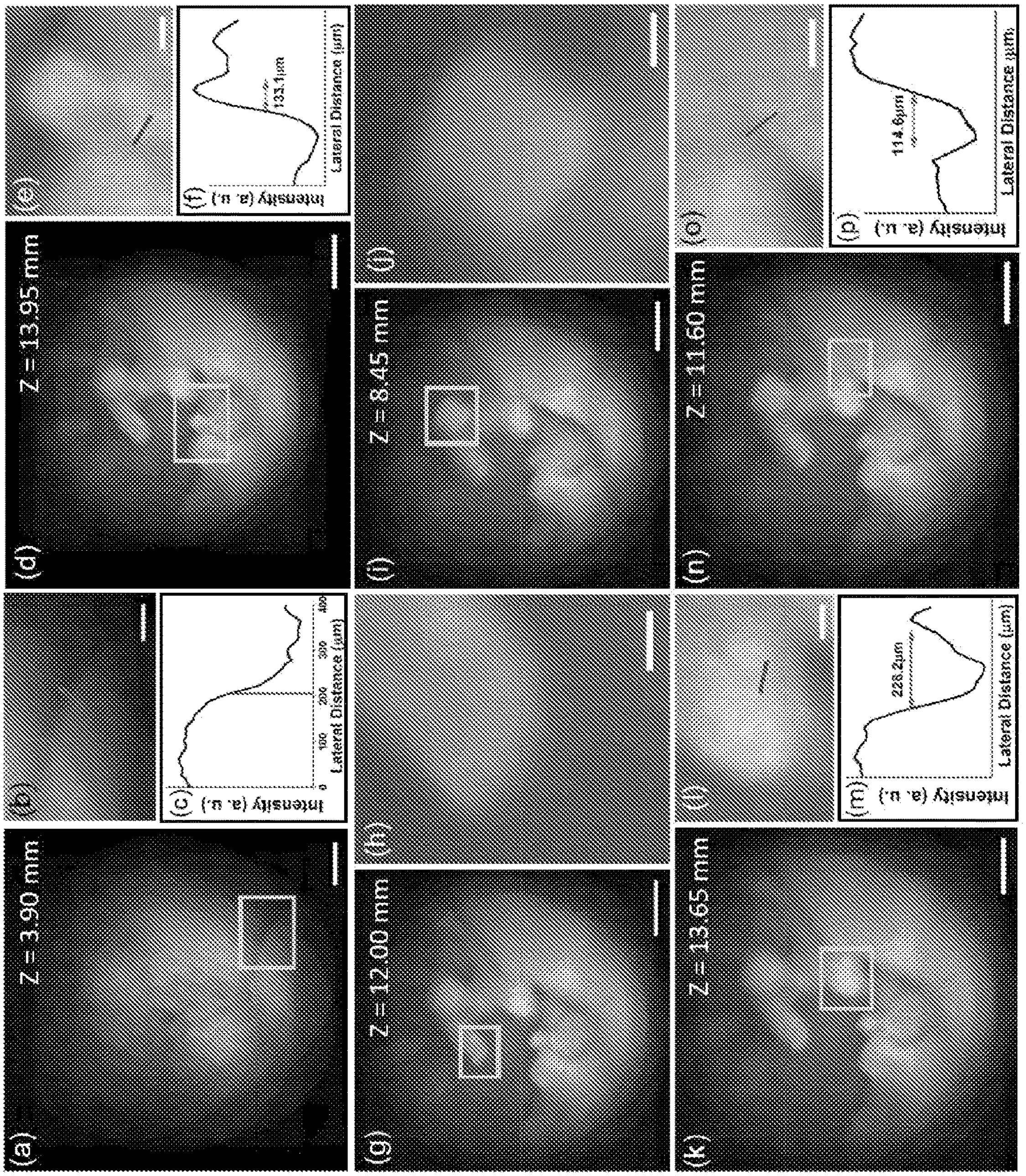
FIGS. 17(*a*)-(*p*) show an imaging phantom heart model.

FIG. 17 shows an imaging phantom heart model. FIGS. 17(*a*), (*d*), (*g*), (*i*), (*k*), and (*n*) are full field-of-view reconstruction slices at various depths z=3.90, 13.95, 12.00, 8.45, 13.65, 11.60 mm from the tip of the endoscope, respectively. FIGS. 17(*b*), (*e*), (*h*), (*j*), (*l*), and (*o*) are corresponding zoomed-in images of the boxed regions of FIGS. 17 (*a*), (*d*), (*g*), (*i*), (*k*), (*n*), respectively. FIGS. 17 (*c*), (*f*), (*m*), and (*p*) show intensity profiles plotted along the red bars in FIGS. 17(*b*), (*e*), (*l*), and (*o*), respectively. The red line in FIG. 17(*c*) indicates the region of the steepest intensity profile. Scale bars: 1.5 mm (FIG. 14(*a*)), 4.0 mm (FIG. 17 (*d*)), 3.5 mm (FIG. 17(*g*)), 2.5 mm (FIG. 17(*i*)), 3.0 mm (FIGS. 17(*k*) and (*n*)), 0.5 mm (FIGS. 17(*b*), (*e*), (*h*), (*j*), (*l*), and (*o*)).

Lastly, we validated the performance of the GLAM system for phantom organs that contain fine features at various axial positions. In particular, the anatomical structures within a 3D printed heart model were imaged (FIG. 17). With the light-field acquisition, we reconstructed the volume of the model and generated the synthesized stack slices (e.g., FIGS. 17(*a*) and (*b*) at z=3.90 mm from the tip of the endoscope). Here, we finely determined the depth of the features by locating the reconstruction stack slice with the steepest slope in the intensity plot (e.g., FIG. 17(*c*)). For example, we selected several reconstructed features at the depths z=13.95 mm (FIGS. 17(*d*) and (*e*)), 12.00 mm (FIGS. 17(*g*) and 17(*h*)), and 8.45 mm (FIGS. 17(*i*) and (*j*)). In comparison, the digital caliper measurement of these features resulted in corresponding physical distances at 13.92 mm, 11.72 mm, and 8.26 mm, indicating good agreement of the quantitative depth rendering using GLAM. Furthermore, the structures of the heart model with feature sizes of 100-200 m can be well resolved (FIGS. 17(*f*), (*m*), and (*p*)), consistent with the prior calibrated lateral resolution of ~100 μm at these corresponding depths (FIGS. 9 and 13).

Laser-Speckle Integrated Endoscope

Laser speckle is an interference pattern produced by light reflected or scattered from different parts of the illuminated surface. If the surface is rough (surface height variations larger than the wavelength of the laser light used), light from different parts of the surface within a resolution cell (the area just resolved by the optical system imaging the surface) traverses different optical path lengths to reach the image plane. (In the case of an observer looking at a laser-illuminated surface, the resolution cell is the resolution limit of the eye and the image plane is the retina.) The resulting intensity at a given point on the image is determined by the superposition of all waves arriving at that point. If the resultant amplitude is zero because all the individual waves cancel out, a dark speckle is seen at the point; if all the waves arrive at the point in phase, an intensity maximum is observed.

Figure 18A:
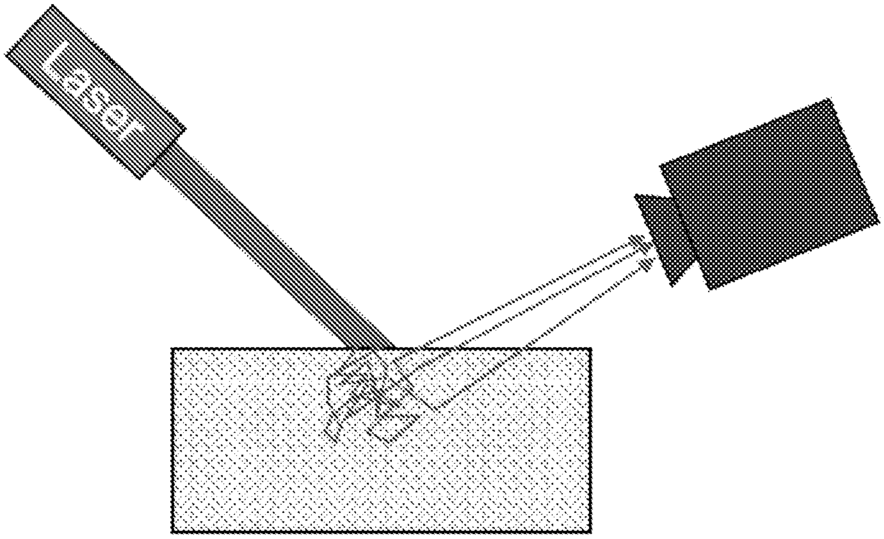
FIGS. 18(*a*) and 18(*b*) illustrate laser speckle contrast imaging.
Figure 18B:
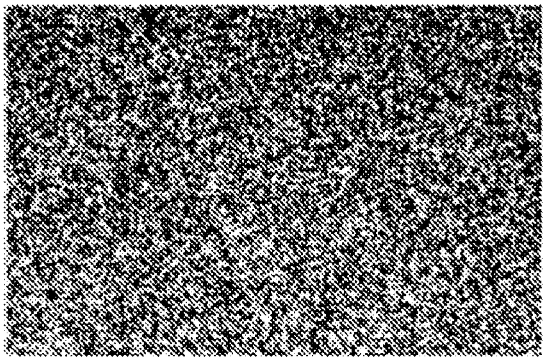
Figure 19A:
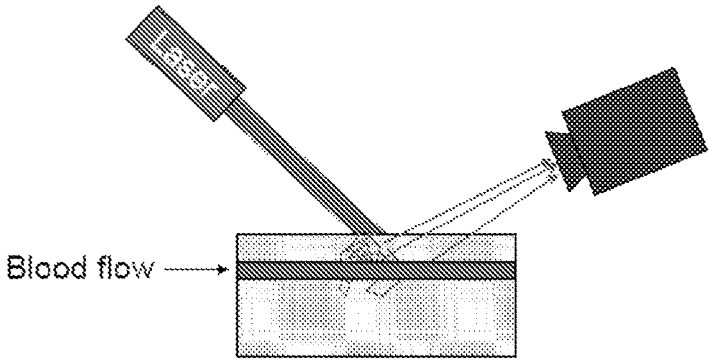
FIG. 19(*a*) illustrates the illumination of a non-static scattering medium and imaging, and FIG. 19(*b*) illustrates the imaged scatter pattern.
Figure 19B:
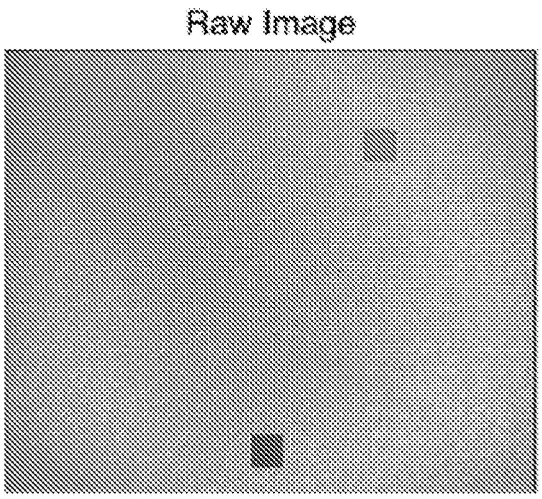
Figure 20:
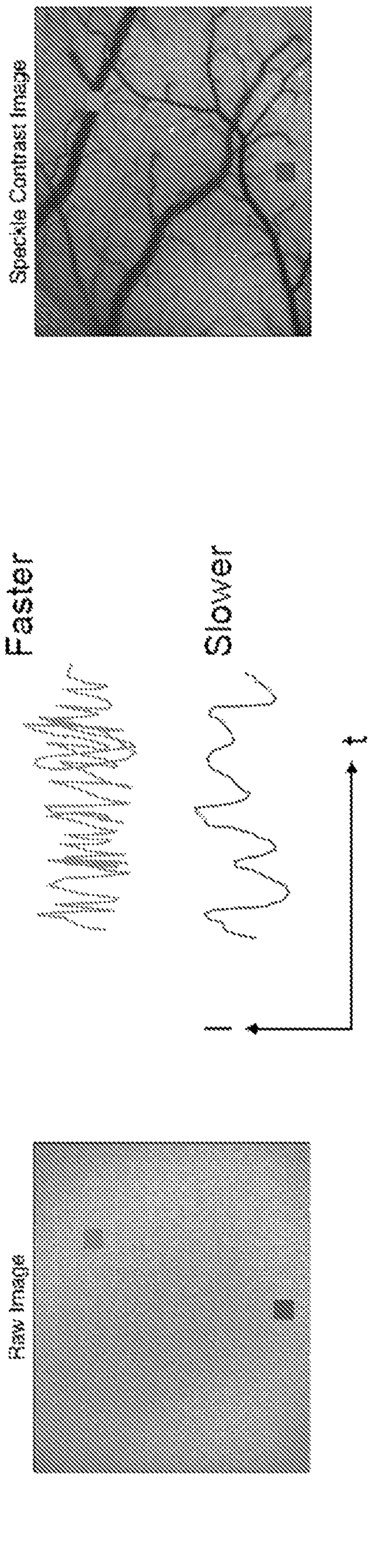
FIG. 20 illustrates the rate of fluctuation is proportional to the underlying scattering image.

FIGS. 18(*a*) and 18(*b*) illustrate laser speckle contrast imaging. As illustrated, a coherent light source (such as a laser) shone on a static scattering medium produces a static speckle pattern. FIG. 18(*a*) illustrates the illumination of a static scattering medium and imaging, and FIG. 18(*b*) illustrates the imaged scatter pattern. As illustrated in FIGS. 19(*a*) and 19(*b*), if that same coherent light source is shone on a non-static scattering medium (such as blood flow), the resulting speckle pattern changes. FIG. 19(*a*) illustrates illumination of a non-static scattering medium and imaging, and FIG. 19(*b*) illustrates the imaged scatter pattern. As illustrated in FIG. 20, the rate of fluctuation is proportional to the underlying scattering image. Accordingly, laser speckle contrast imaging can be used to determine blood perfusion and flow, locate vasculature, and help identify intraoperative cues not visible to the naked eye. This laser speckle can be integrated with the endoscope probe described herein. For example, a center GRIN lens or light source can be replaced by a coherent light source to provide the laser speckle imaging data. E.g., a laser diode can be provided as the coherent light source.

Discussion

Physicians are accustomed to endoscopes that provide two-dimensional images originating from three-dimensional structures. However, surgeons' access to topological information in the axial dimension of the surgical field facilitated by rigid 3D endoscopy has been reported to reduce operation times and errors, especially in surgeries involving significant in-depth extension or 3D tissue complexity. Furthermore, 3D endoscopy has shown promise for improving the learning experience of medical trainees.

Current clinical technologies incorporate stereoscopic imaging principles, in which two apertures record the tissue landscape simultaneously. The surgeon relays this information as a 2D image on either a head-mounted display or a specialized monitor that can be converted to a 3D perception using polarized eyewear. While demonstrating the power of restoring depth perception to minimally invasive surgery, stereoscopic approaches suffer ergonomic and analytical downsides. Practically, the eyewear can cause dizziness and headaches after long periods of use, with some surgeons reporting excessive strain with the stereoscopic systems compared to conventional 2D endoscopy, even though operation times can be reduced. Additionally, stereoscopic vision lacks quantitative 3D recording and reconstruction for intraoperative decisions, subsequent diagnostics, or data storage. As a result, surgeries may require other imaging procedures, such as micro-CT or MRI, to quantify the 3D morphology of tissue. Indeed, acquiring quantitative volumetric information during surgical procedures has significant implications for diagnostics, treatment, and integration with digital and robotic devices.

In contrast, to achieve 3D reconstruction without eyewear, computational approaches to stereoscopic endoscopy such as deformable shape-from-motion and shape-from-shading, have been proposed to quantify the 3D surface. However, these algorithms are highly sample-dependent and may suffer from reduced temporal resolution due to required probe translation. Other quantitative approaches to stereoscopic imaging using epipolar geometry and the pinhole camera model have been shown to attain quantitative results but remain limited by the nonuniform field of view due to the use of only two apertures.

Light-field imaging is an optical methodology that addresses the limitations of the two-aperture approach in stereoscopic imaging. Light-field imaging, often used in 3D microscopy, is characterized by sampling the 2D spatial and 2D angular components of the light field with a lens or camera array. For example, this approach has been applied to endoscopy by Orth and colleagues, who demonstrated that 3D light-field imaging could be obtained with a flexible multi-mode fiber bundle. In contrast, rigid light-field endoscopy and otoscopy systems have also been proposed, utilizing microlenses or tunable electro-optic lens arrays, both of which, however, lead to a significant reduction in lateral resolution. Therefore, there remains a demand for lens-based 3D endoscopy techniques that maintain high spatial resolution while providing quantitative depth information.

In this work, we demonstrate fast, 3D, multi-color microendoscopic imaging achieved by using a hexagonal gradient index (GRIN) lens array. This GRIN lens array microendoscopy system, or GLAM, provides a quantitative 3D imaging methodology with a high lateral and axial resolution. With the capability to detect the depth of features with sub-millimeter accuracy, GLAM is designed to meet many of the functional and physical requirements of a practical endoscope, including a small-diameter stainless steel shaft, built-in illumination, and multi-color imaging. With this combination of optical functionality and realistic endoscope design, GLAM demonstrates that quantitative 3D light-field imaging using GRIN lenses can be practically applied to rigid endoscopy, paving the way for future development using this optical paradigm. We expect GLAM to provide a necessary prototype to increase operative safety and efficiency with further implications on improving instrument control during robotic surgery. FIG. 21 illustrates a comparison of actual reconstruction according to a prototype (RayOpticsRecon) of the presently described device with respect to other devices.

Additional experimental results and examples are provided herein, each of which is incorporated by reference herein in its entirety. The presently described system and methods endeavor to adapt to and enhance 3D human visual navigation into various complex microenvironments, to provide quantitative and machine-intelligent recognition and display of 3D anatomies, allow for "Glasses-free", real-time guidance and intervention, and lead to breakthroughs in patient care, clinical screening, diagnostics, decision-making, as well as medical training. Embodiments described herein utilize clinically-relevant design parameters: compact light-field propagation and a LED-based array of fiber optics for uniform illumination.

It should be appreciated that the logical operations described above can be implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as state operations, acts, or modules. These operations, acts, and/or modules can be implemented in software, in firmware, in special purpose digital logic, in hardware, and any combination thereof. It should also be appreciated that more or fewer operations can be performed than shown in the figures and described herein. These operations can also be performed in a different order than those described herein.

Figure 22:
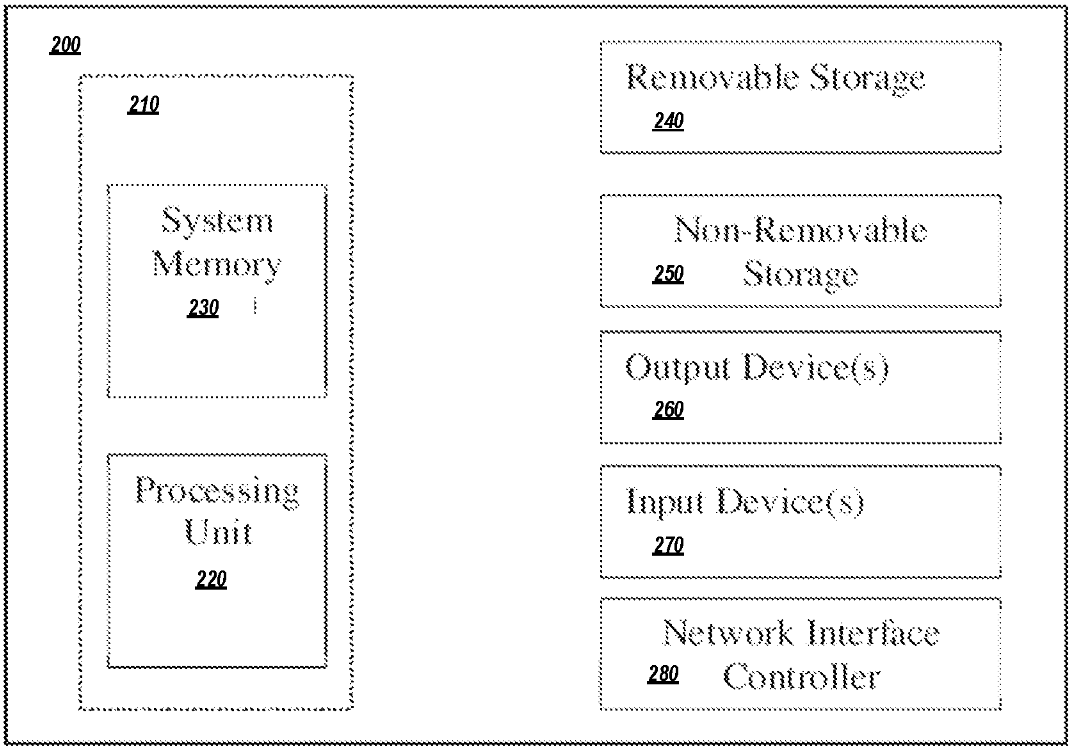
FIG. 22 shows an illustrative computer architecture for a computer system 200 capable of executing the software components that can use the output of the exemplary method described herein.

In addition to the various microendoscopy systems and probes discussed herein, FIG. 22 shows an illustrative computer architecture for a computer system 200 capable of executing the software components that can use the output of the exemplary method described herein. The computer architecture shown in FIG. 22 illustrates an example computer system configuration, and the computer 200 can be utilized to execute any aspects of the components and/or modules presented herein described as executing on the analysis system or any components in communication therewith.

In an embodiment, the computing device 200 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 200 to provide the functionality of a number of servers that is not directly bound to the number of computers in the computing device 200. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third-party provider. Some cloud computing environments may comprise cloud computing resources owned and operated by the enterprise as well as cloud computing resources hired and/or leased from a third-party provider.

In its most basic configuration, computing device 200 typically includes at least one processing unit 220 and system memory 230. Depending on the exact configuration and type of computing device, system memory 230 may be volatile (such as random-access memory (RAM)), non-volatile (such as read-only memory (ROM), flash memory, etc.), or some combination of the two.

This most basic configuration is illustrated in FIG. 22 by dashed line 210. The processing unit 220 may be a standard programmable processor that performs arithmetic and logic operations necessary for operation of the computing device 200. While only one processing unit 220 is shown, multiple processors may be present. As used herein, processing unit and processor refers to a physical hardware device that executes encoded instructions for performing functions on inputs and creating outputs, including, for example, but not limited to, microprocessors (MCUs), microcontrollers, graphical processing units (GPUs), and application specific circuits (ASICs). Thus, while instructions may be discussed as executed by a processor, the instructions may be executed simultaneously, serially, or otherwise executed by one or multiple processors. The computing device 200 may also include a bus or other communication mechanism for communicating information among various components of the computing device 200.

Computing device 200 may have additional features/functionality. For example, computing device 200 may include additional storage such as removable storage 240 and non-removable storage 250, including, but not limited to, magnetic or optical disks or tapes. Computing device 200 may also contain network connection(s) 280 that allow the device to communicate with other devices, such as over the communication pathways described herein. The network connection(s) 280 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 200 may also have input device(s) 270 such as keyboards, keypads, switches, dials, mice, track balls, touch screens, voice recognizers, card readers, paper tape readers, or other well-known input devices. Output device(s) 260 such as printers, video monitors, liquid crystal displays (LCDs), touch screen displays, displays, speakers, etc. may also be included. The additional devices may be connected to the bus in order to facilitate communication of data among the components of the computing device 200. All these devices are well known in the art and need not be discussed at length here.

The processing unit 220 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 220 for execution. Example tangible, computer-readable media may include, but is not limited to, volatile media, non-volatile media, removable media and non-removable media implemented in any method or technology for storage of information such as computer readable instructions, data structures, program modules or other data. System memory 230, removable storage 240, and non-removable storage 250 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In light of the above, it should be appreciated that many types of physical transformations take place in the computer architecture 200 in order to store and execute the software components presented herein. It also should be appreciated that the computer architecture 200 may include other types of computing devices, including hand-held computers, embedded computer systems, personal digital assistants, and other types of computing devices known to those skilled in the art. It is also contemplated that the computer architecture 200 may not include all of the components shown in FIG. 2X, may include other components that are not explicitly shown in FIG. 22, or may utilize an architecture different than that shown in FIG. 22.

In an example implementation, the processing unit 220 may execute program code stored in the system memory 230. For example, the bus may carry data to the system memory 230, from which the processing unit 220 receives and executes instructions. The data received by the system memory 230 may optionally be stored on the removable storage 240 or the non-removable storage 250 before or after execution by the processing unit 220.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Moreover, the various components may be in communication via wireless and/or hardwire or other desirable and available communication means, systems and hardware. Moreover, various components and modules may be substituted with other modules or components that provide similar functions.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include from the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. An optical microendoscopy system, comprising:

an endoscopic probe, the probe having a plurality of integrated fiber optics for uniform illumination and an array of gradient index (GRIN) lenses configured to capture a reflected light field from one or more on-axis sampling of the reflected light field and two or more off-axis sampling of the reflected light field; and an image processing unit configured to receive the reflected light field from the endoscopic probe to reconstruct an image using a ray-optics reconstruction operation, wherein the image processing unit is configured to employ point-spread function (PSF) calibration in the ray-optics reconstruction operation, and wherein the point-spread function (PSF) calibration involves fitting an experimental depth-dependent magnification function M (z) with a ray-optics model of magnification.

2. The optical microendoscopy system of claim 1, wherein the captured reflected light field comprises 6 off-axis samples.

3. The optical microendoscopy system of claim 1, wherein the plurality of integrated fiber optics comprises 3 or more fibers embedded within an endoscopic probe core, each having an illumination output.

4. The optical microendoscopy system of claim 1, wherein each of the fiber optics comprises an illumination output at an end of the endoscopic probe, wherein the illumination outputs are distributed equally at the end of the endoscopic probe.

5. The optical microendoscopy system of claim 1, wherein the GRIN lens array comprises 6 GRIN lenses.

6. The optical microendoscopy system of claim 5, wherein the 6 GRIN lenses are positioned in a hexagonal array at an end of the endoscopic probe, and wherein the system further includes a seventh GRIN lens at a center of the hexagonal array at the end of the endoscopic probe.

7. The optical microendoscopy system of claim 6, further comprising an illumination output of one of the integrated fiber optics at a center of the hexagonal array at the end of the endoscopic probe.

8. The optical microendoscopy system of claim 1, wherein GRIN lenses of the GRIN lens array alternate with illumination outputs of individual ones of the integrated fiber optic at an end of the endoscopic probe.

9. The optical microendoscopy system of claim 1, wherein a first subset of the GRIN lenses in the array comprises a first property and wherein a second subset of the GRIN lenses in the array comprises a second property different from the first.

10. The optical microendoscopy system of claim 9, wherein the first property is a first polarization and the second property is a second polarization.

11. The optical microendoscopy system of claim 9, further comprising a third subset of GRIN lenses comprise a third property different from the first property and the second property.

12. The optical microendoscopy system of claim 11, wherein the first property, the second property, and the third property are selected from polarization, fluorescence in addition to bright field, wavelength, and time-gated light.

13. The optical microendoscopy system of claim 1, wherein the integrated fiber optics comprises LED light sources.

14. The optical microendoscopy system of claim 1, wherein the endoscopic probe comprises a Hopkins rod lens or a gradient index relay.

15. The optical microendoscopy system of claim 1, further comprising a laser light source at an end of the endoscopic probe and a camera for receiving reflected laser light.

16. A method of operating an optical microendoscopy system, the method comprising:

providing illumination from an end of an endoscopic probe, the endoscopic probe having a plurality of integrated fiber optic illumination sources for uniform illumination;

capturing a reflected light field, for light-field imaging, through an array of gradient index (GRIN) lenses, including (i) one or more on-axis sampling of the reflected light field and (ii) two or more off-axis sampling of the reflected light field; and reconstructing an image, via a ray-optics reconstruction algorithm employing a point-spread function (PSF) calibration, using (i) the one or more on-axis sampling of the reflected light field and (ii) the two or more off-axis sampling of the reflected light field, wherein the point-spread function (PSF) calibration involves fitting an experimental depth-dependent magnification function M (z) with a ray-optics model of magnification.

17. An endoscopic probe, comprising:

a plurality of integrated fiber optics for uniform illumination and an array of gradient index (GRIN) lenses configured to capture a reflected light field from one or more on-axis sampling of the reflected light field and two or more off-axis sampling of the reflected light field, wherein the endoscopic probe is operatively coupled to an image processing unit configured to receive, from the endoscopic probe, the reflected light field to reconstruct an image using a ray-optics reconstruction operation, wherein the image processing unit is configured to employ point-spread function (PSF) calibration in the ray-optics reconstruction operation, and wherein the point-spread function (PSF) calibration involves fitting an experimental depth-dependent magnification function M (z) with a ray-optics model of magnification.

* * * * *